(12) United States Patent
Zass et al.

(10) Patent No.: US 10,433,052 B2
(45) Date of Patent: Oct. 1, 2019

(54) SYSTEM AND METHOD FOR IDENTIFYING SPEECH PROSODY

(71) Applicants: Ron Zass, Kiryat Tivon (IL); Yotam Zass Rozenfeld, Kiryat Tivon (IL)

(72) Inventors: Ron Zass, Kiryat Tivon (IL); Yotam Zass Rozenfeld, Kiryat Tivon (IL)

(*) Notice: Subject to any disclaimer, the term of this patent is extended or adjusted under 35 U.S.C. 154(b) by 16 days.

(21) Appl. No.: 15/650,939

(22) Filed: Jul. 16, 2017

(65) Prior Publication Data

US 2018/0018975 A1 Jan. 18, 2018

Related U.S. Application Data

(60) Provisional application No. 62/363,261, filed on Jul. 16, 2016, provisional application No. 62/444,709, (Continued)

(51) Int. Cl.

| | |
|---|---|
| *G10L 17/26* | (2013.01) |
| *H04R 1/40* | (2006.01) |
| *H04R 1/26* | (2006.01) |
| *G06K 9/00* | (2006.01) |
| *G16H 50/70* | (2018.01) |
| *A61N 1/36* | (2006.01) |
| *G10L 17/00* | (2013.01) |
| *G10L 21/02* | (2013.01) |

(Continued)

(52) U.S. Cl.
CPC .............. *H04R 1/406* (2013.01); *A61B 5/16* (2013.01); *A61N 1/36082* (2013.01); *G06F 17/20* (2013.01); *G06F 17/21* (2013.01); *G06K 9/00275* (2013.01); *G06K 9/00369* (2013.01); *G10L 15/1822* (2013.01); *G10L 17/005* (2013.01); *G10L 17/26* (2013.01); *G10L 21/0205* (2013.01); *G10L 21/028* (2013.01); *G10L 21/0224* (2013.01); *G10L 25/63* (2013.01); *G10L 25/72* (2013.01); *G16H 50/70* (2018.01); *H04R 1/265* (2013.01); *H04R 3/005* (2013.01); *H04R 25/407* (2013.01); *A61B 5/02055* (2013.01); *A61B 5/1114* (2013.01); *A61B 5/1128* (2013.01); *A61B 2562/0204* (2013.01); *A61B 2562/0219* (2013.01); *G01N 2800/28* (2013.01); *G06K 9/00228* (2013.01); *G06K 9/00362* (2013.01); *G06K 9/46* (2013.01); *H04R 5/0335* (2013.01); *H04R 2201/023* (2013.01); *H04R 2225/43* (2013.01)

(58) Field of Classification Search
CPC ......... G10L 15/22; G10L 15/08; G10L 15/26; G10L 17/26; G10L 25/63; G10L 15/1807
See application file for complete search history.

(56) References Cited

U.S. PATENT DOCUMENTS

| | | | |
|---|---|---|---|
| 6,882,971 B2 * | 4/2005 | Craner .................. | H04M 1/247 704/246 |
| 10,084,920 B1 * | 9/2018 | Gainsboro ............ | H04M 3/568 |

(Continued)

*Primary Examiner* — Richemond Dorvil
*Assistant Examiner* — Mark Villena

(57) ABSTRACT

System and method for analyzing audio data are provided. The audio data may be analyzed to identify speech prosody. For example, the audio data may be analyzed to select a portion of the audio data containing speech produced by a first speaker. The audio data may be further analyzed to identify speech prosody of the speech within the selected portion. Feedbacks and reports may be provided based on the identified speech prosody.

25 Claims, 14 Drawing Sheets

Related U.S. Application Data filed on Jan. 10, 2017, provisional application No. 62/460,783, filed on Feb. 18, 2017.

(51) Int. Cl.

| | |
|---|---|
| *G10L 21/028* | (2013.01) |
| *H04R 3/00* | (2006.01) |
| *H04R 25/00* | (2006.01) |
| *G10L 25/72* | (2013.01) |
| *G10L 15/18* | (2013.01) |
| *G06F 17/21* | (2006.01) |
| *G06F 17/20* | (2006.01) |
| *G10L 21/0224* | (2013.01) |
| *G10L 25/63* | (2013.01) |
| *A61B 5/16* | (2006.01) |
| *G06K 9/46* | (2006.01) |
| *H04R 5/033* | (2006.01) |
| *A61B 5/0205* | (2006.01) |
| *A61B 5/11* | (2006.01) |

(56) References Cited

U.S. PATENT DOCUMENTS

| | | | |
|---|---|---|---|
| 2010/0250257 A1* | 9/2010 | Hirose | G10L 13/033 704/278 |
| 2010/0262419 A1* | 10/2010 | De Bruijn | G10L 15/1822 704/9 |
| 2012/0215532 A1* | 8/2012 | Foo | H04R 25/505 704/235 |
| 2014/0122077 A1* | 5/2014 | Nishikawa | G10L 17/04 704/249 |
| 2014/0247926 A1* | 9/2014 | Gainsboro | H04M 3/2281 379/88.01 |
| 2015/0099946 A1* | 4/2015 | Sahin | A61B 5/16 600/301 |
| 2015/0334346 A1* | 11/2015 | Cheatham, III | H04N 7/147 348/14.05 |
| 2015/0373477 A1* | 12/2015 | Norris | H04M 1/72572 381/303 |
| 2016/0064002 A1* | 3/2016 | Kim | G10L 15/22 704/246 |
| 2017/0041699 A1* | 2/2017 | Mackellar | H04R 1/1075 |
| 2017/0076000 A1* | 3/2017 | Ashoori | G06F 17/30867 |

\* cited by examiner

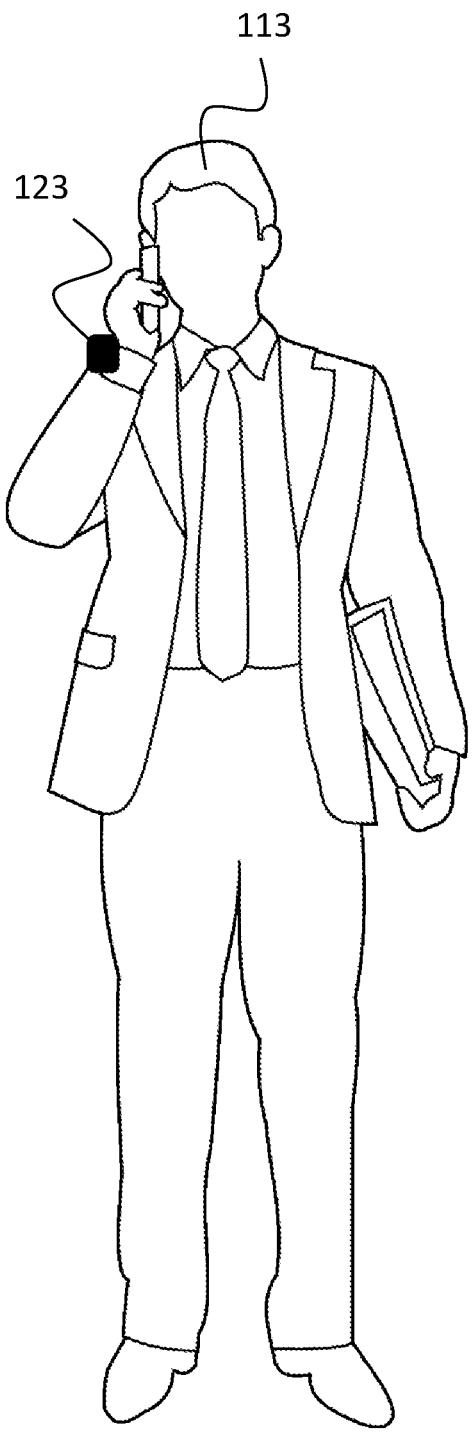
FIG. 1C  FIG. 1D

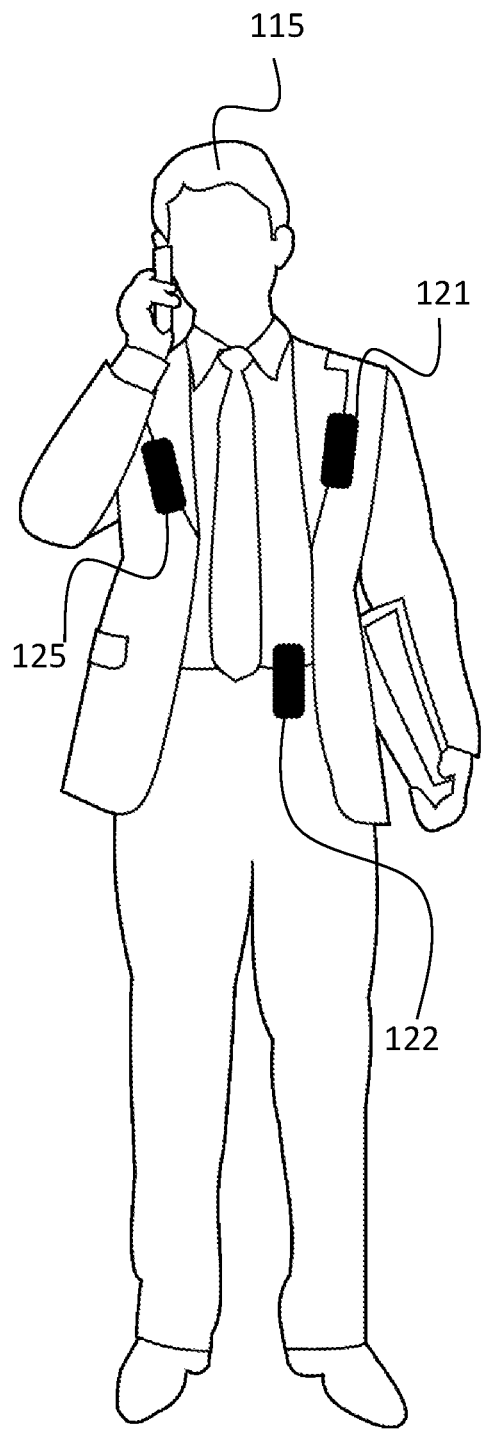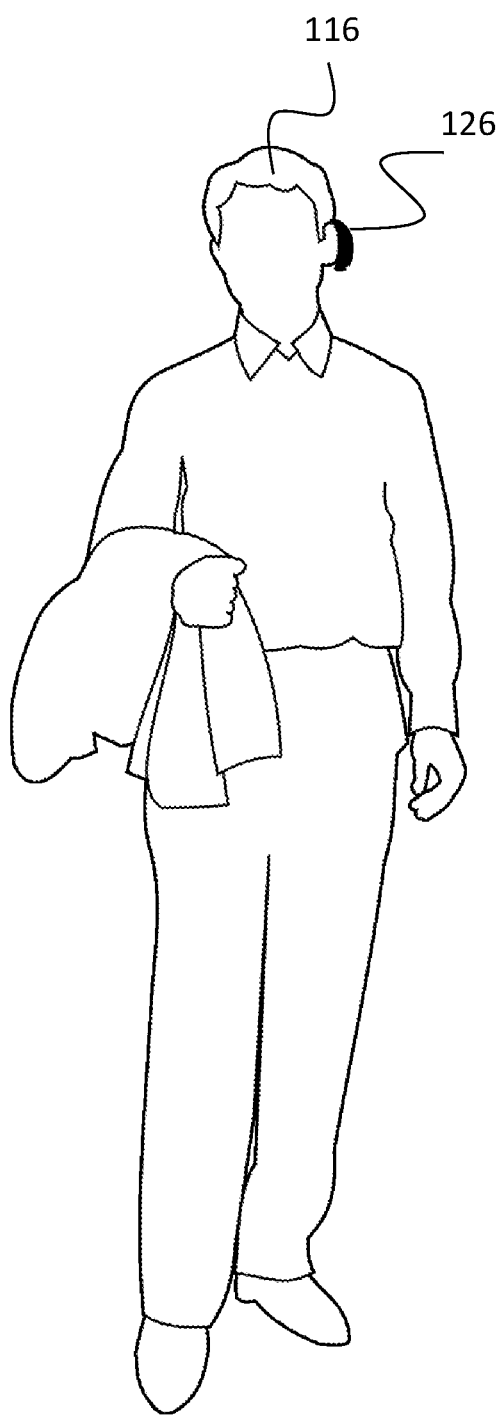
FIG. 1E             FIG. 1F

SYSTEM AND METHOD FOR IDENTIFYING SPEECH PROSODY

CROSS REFERENCES TO RELATED APPLICATIONS

This application claims the benefit of priority of U.S. Provisional Patent Application No. 62/363,261, filed on Jul. 16, 2016, U.S. Provisional Patent Application No. 62/444,709, filed on Jan. 10, 2017, and U.S. Provisional Patent Application No. 62/460,783, filed on Feb. 18, 2017, the disclosures of which incorporated herein by reference in their entirety.

BACKGROUND

Technological Field

The disclosed embodiments generally relate to systems and methods for processing audio. More particularly, the disclosed embodiments relate to systems and methods for processing audio to identify speech prosody.

Background Information

Audio as well as other sensors are now part of numerous devices, from intelligent personal assistant devices to mobile phones, and the availability of audio data and other information produced by these devices is increasing.

Cluttering, also known as tachyphemia or tachyphrasia, is a communication disorder characterized by rapid rate of speech, erratic speaking rhythm, loss of fluency, frequent pauses, and so forth. Aprosodia is a neurological condition characterized by difficult or inability to properly convey or interpret emotional prosody. Dysprosody is a neurological disorder characterized by impairment in one or more of the prosodic functions. Apraxia of speech is a communication disorder characterized by difficulty in speech production, specifically with sequencing and forming sounds, impaired speech prosody, and in particular impaired speech rhythm. Prosody may refer to variation in rhythm, pitch, stress, intonation, accent, vocal quality, intensity, tempo, flatness, melody, pauses, timing, and so forth. Impaired prosodic functions are also a possible symptom of several other neurological and psychiatric conditions, including: autism, Asperger syndrome, schizophrenia, clinical depression, aphasia, neurodegenerative conditions, and so forth.

SUMMARY

In some embodiments, a system and a method for capturing and processing audio data from the environment of a person are provided. The audio data may be analyzed. In some examples, feedbacks may be provided, for example with regard to conversations detected in the audio data. In some examples, reports may be produced, for example based on conversations detected in the audio data. In some embodiments the system may include a wearable apparatus configured to be worn by a wearer.

In some embodiments, additional input sensors may be used, for example to detect and interpret nonverbal communication. For example, the additional input sensors may include image sensors.

In some embodiments, a method and a system for identifying speech prosody are provided. Audio data captured by audio sensors may be obtained. The audio data may be analyzed to identify one or more portions of the audio data associated with a speaker. The audio data may be analyzed to obtain prosodic information associated with the one or more portions.

BRIEF DESCRIPTION OF THE DRAWINGS

FIGS. 1A, 1B, 1C, 1D, 1E and 1F are schematic illustrations of some examples of a user wearing a wearable apparatus.

DESCRIPTION

Figure 1A:
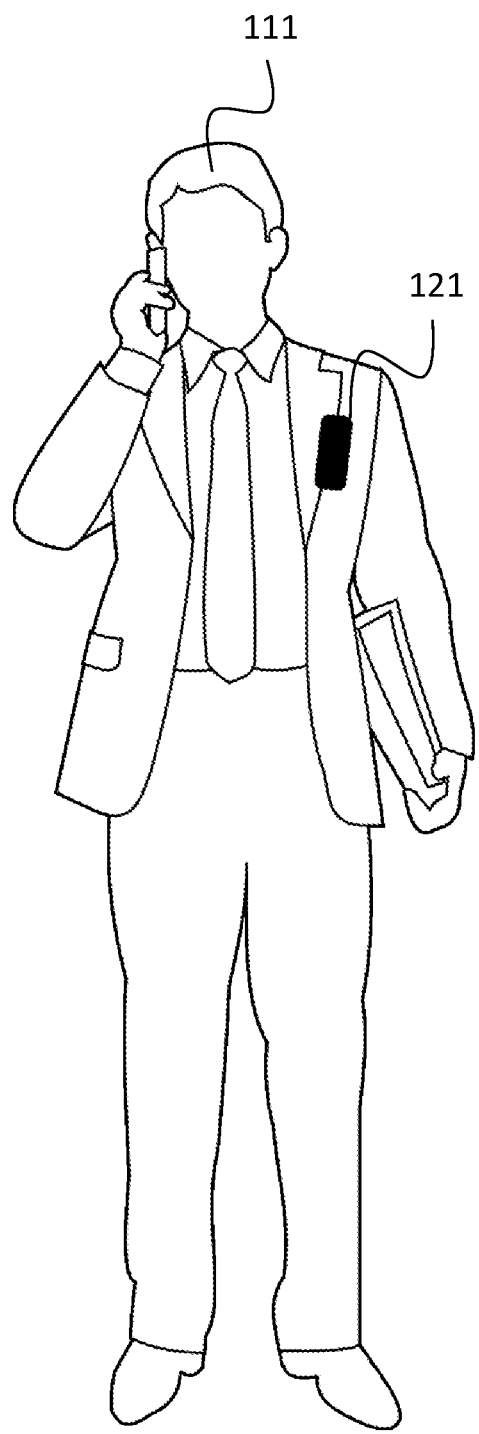

Unless specifically stated otherwise, as apparent from the following discussions, it is appreciated that throughout the specification discussions utilizing terms such as "processing", "calculating", "computing", "determining", "generating", "setting", "configuring", "selecting", "defining", "applying", "obtaining", "monitoring", "providing", "identifying", "segmenting", "classifying", "analyzing", "associating", "extracting", "storing", "receiving", "transmitting", or the like, include action and/or processes of a computer that manipulate and/or transform data into other data, said data represented as physical quantities, for example such as electronic quantities, and/or said data representing the physical objects.

The terms "computer", "processor", "controller", "processing unit", "computing unit", "processing device", and "processing module" should be expansively construed to cover any kind of electronic device, component or unit with data processing capabilities, including, by way of non-limiting example, a personal computer, a wearable computer, a tablet, a smartphone, a server, a computing system, a cloud computing platform, a communication device, a processor (for example, digital signal processor (DSP), an image signal processor (ISR), a microcontroller, a field programmable gate array (FPGA), an application specific integrated circuit (ASIC), a central processing unit (CPA), a graphics processing unit (GPU), a visual processing unit (VPU), and so on), possibly with embedded memory, a single core processor, a multi core processor, a core within a processor, any other electronic computing device, or any combination of the above.

The operations in accordance with the teachings herein may be performed by a computer specially constructed or programmed to perform the described functions.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) may be included in at least one embodiment of the presently disclosed subject matter. Thus the appearance of the phrase "one case", "some cases", "other cases" or variants thereof does not necessarily refer to the same embodiment(s). As used herein, the term "and/or" includes any and all combinations of one or more of the associated listed items.

It is appreciated that certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable subcombination.

One or more stages illustrated in the drawings may be executed in a different order and/or one or more groups of stages may be executed simultaneously and vice versa. The drawings illustrate a general schematic of the system architecture in accordance embodiments of the presently disclosed subject matter. Each module in the drawings can be made up of any combination of software, hardware and/or firmware that performs the functions as defined and explained herein. The modules in the drawings may be centralized in one location or dispersed over more than one location.

It should be noted that some examples of the presently disclosed subject matter are not limited in application to the details of construction and the arrangement of the components set forth in the following description or illustrated in the drawings. The invention can be capable of other embodiments or of being practiced or carried out in various ways. Also, it is to be understood that the phraseology and terminology employed herein is for the purpose of description and should not be regarded as limiting. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Wherever possible, the same reference numbers are used in the drawings and the following description to refer to the same or similar parts.

The drawings in this document may not be to any scale. Different drawings may use different scales and different scales can be used even within the same drawing, for example different scales for different views of the same object or different scales for the two adjacent objects.

FIG. 1A is a schematic illustration of an example of user 111 wearing wearable apparatus or a part of a wearable apparatus 121. In this example, wearable apparatus or a part of a wearable apparatus 121 may be physically connected or integral to a garment, and user 111 may wear the garment.

Figure 1B:
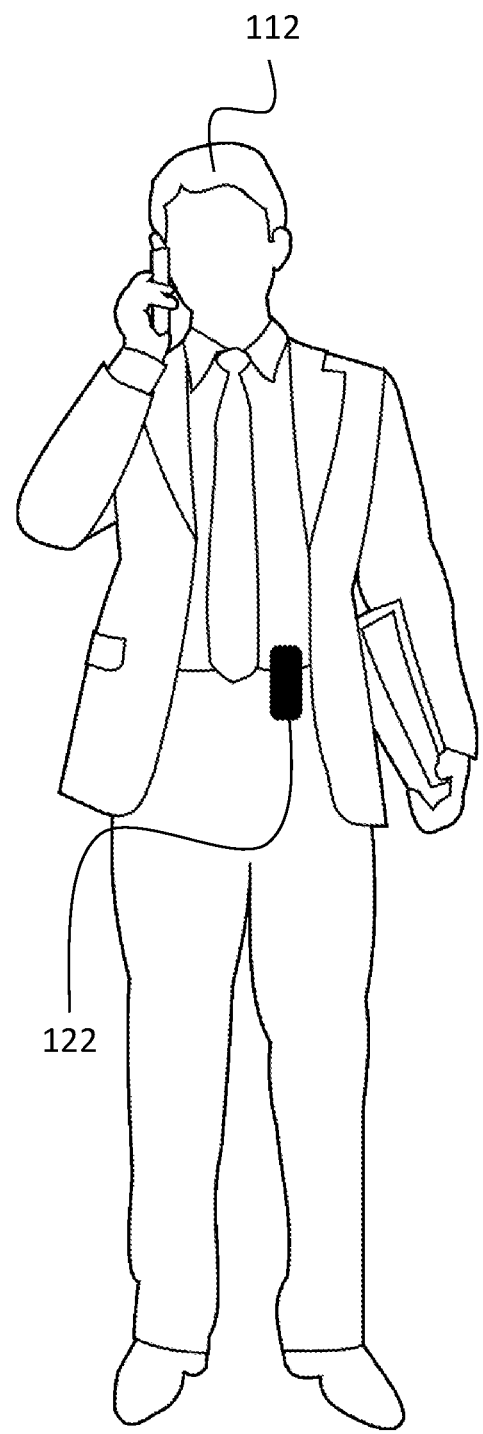

FIG. 1B is a schematic illustration of an example of user 112 wearing wearable apparatus or a part of a wearable apparatus 122. In this example, wearable apparatus or a part of a wearable apparatus 122 may be physically connected or integral to a belt, and user 112 may wear the belt.

FIG. 1C is a schematic illustration of an example of user 113 wearing wearable apparatus or a part of a wearable apparatus 123. In this example, wearable apparatus or a part of a wearable apparatus 123 may be physically connected or integral to a wrist strap, and user 113 may wear the wrist strap.

FIG. 1D is a schematic illustration of an example of user 114 wearing wearable apparatus or a part of a wearable apparatus 124. In this example, wearable apparatus or a part of a wearable apparatus 124 may be physically connected or integral to a necklace 134, and user 114 may wear necklace 134.

FIG. 1E is a schematic illustration of an example of user 115 wearing wearable apparatus or a part of a wearable apparatus 121, wearable apparatus or a part of a wearable apparatus 122, and wearable apparatus or a part of a wearable apparatus 125. In this example, wearable apparatus or a part of a wearable apparatus 122 may be physically connected or integral to a belt, and user 115 may wear the belt. In this example, wearable apparatus or a part of a wearable apparatus 121 and wearable apparatus or a part of a wearable apparatus 125 may be physically connected or integral to a garment, and user 115 may wear the garment.

FIG. 1F is a schematic illustration of an example of user 116 wearing wearable apparatus or a part of a wearable apparatus 126. In this example, wearable apparatus or a part of a wearable apparatus 126 may be physically connected to an ear of user 116. In some examples, wearable apparatus or a part of a wearable apparatus 126 may be physically connected to the left ear and/or right ear of user 116. In some examples, user 116 may wear two wearable apparatuses 126, where one wearable apparatus 126 may be connected to the left ear of user 116, and the second wearable apparatus 126 may be connected to the right ear of user 116. In some examples, user 116 may wear a wearable apparatus 126 that has at least two separate parts, where one part of wearable apparatus 126 may be connected to the left ear of user 116, and the second part of wearable apparatus 126 may be connected to the right ear of user 116.

In some embodiments, a user may wear one or more wearable apparatuses, such as one or more instances of wearable apparatuses 121, 122, 123, 124, 125, and/or 126. For example, a user may wear one or more wearable apparatuses that are physically connected or integral to a garment of the user, such as wearable apparatus 121 and/or wearable apparatus 125. For example, a user may wear one or more wearable apparatuses that are physically connected or integral to a belt of the user, such as wearable apparatus 122. For example, a user may wear one or more wearable apparatuses that are physically connected or integral to a wrist strap of the user, such as wearable apparatus 123. For example, a user may wear one or more wearable apparatuses that are physically connected or integral to a necklace that the user is wearing, such as wearable apparatus 124. For example, a user may wear one or more wearable apparatuses that are physically connected or integral to the left ear and/or right ear of the user, such as wearable apparatus 126. In some examples, the one or more wearable apparatuses may communicate and/or collaborate with one another. For example, the one or more wearable apparatuses may communicate by wires and/or wirelessly.

In some embodiments, a user may wear a wearable apparatus, and the wearable apparatus may comprise two or more separate parts. For example, the wearable apparatus may comprise parts 121, 122, 123, 124, 125, and/or 126. For example, the wearable apparatus may comprise one or more parts that are physically connected or integral to a garment of the user, such as 121 and/or part 125. For example, the wearable apparatus may comprise one or more parts that are physically connected or integral to a belt of the user, such as part 122. For example, the wearable apparatus may comprise one or more parts that are physically connected or integral to a wrist strap that the user is wearing, such as part 123. For example, the wearable apparatus may comprise one or more parts that are physically connected or integral to a necklace that the user is wearing, such as part 124. For example, the wearable apparatus may comprise one or more parts that are physically connected to the left ear and/or the right ear of the user, such as part 126. In some examples, the separate parts of the wearable apparatus may communicate by wires and/or wirelessly.

Figure 3A:
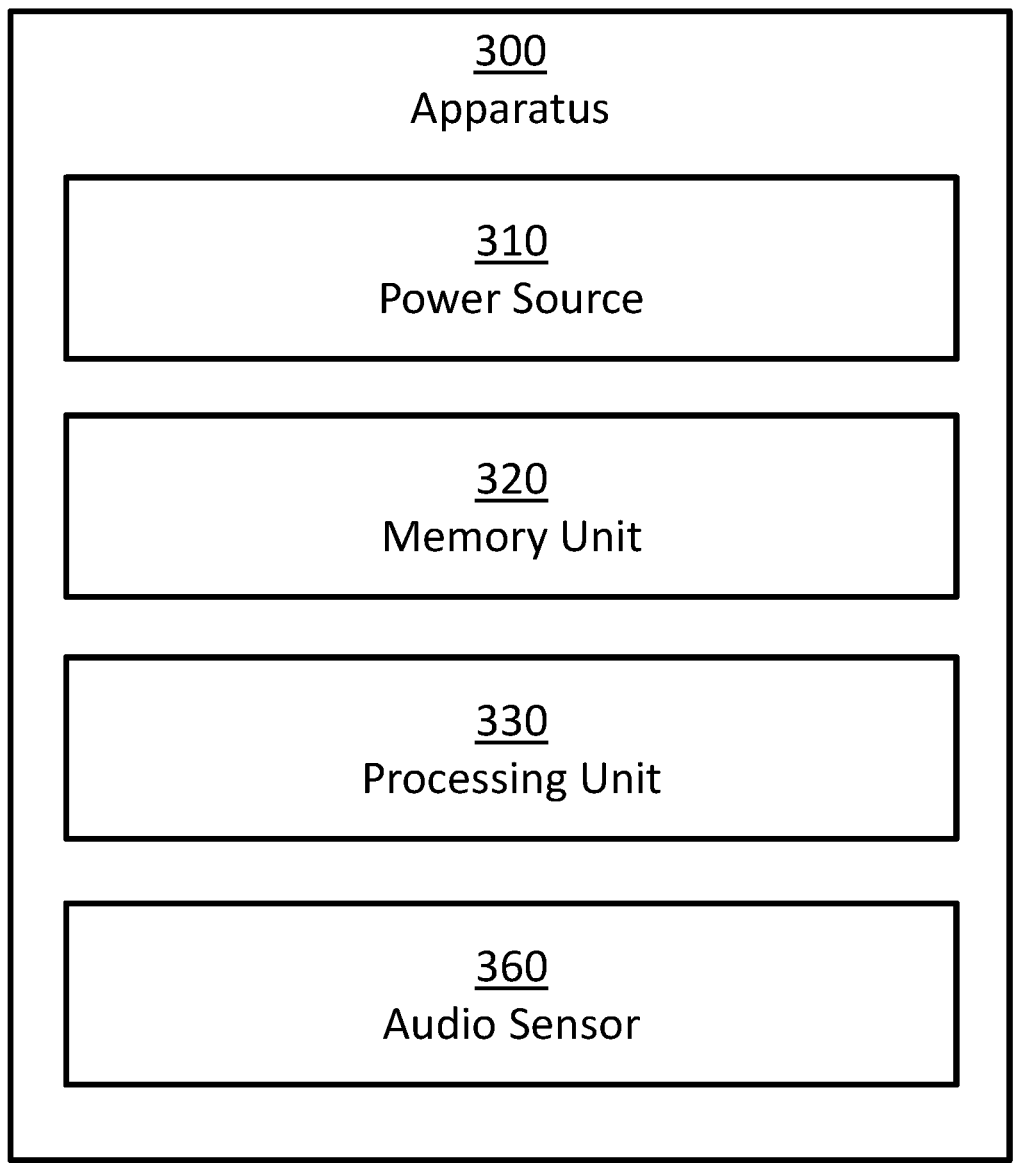
FIGS. 3A and 3B are block diagrams illustrating some possible implementation of an apparatus.
Figure 3B:
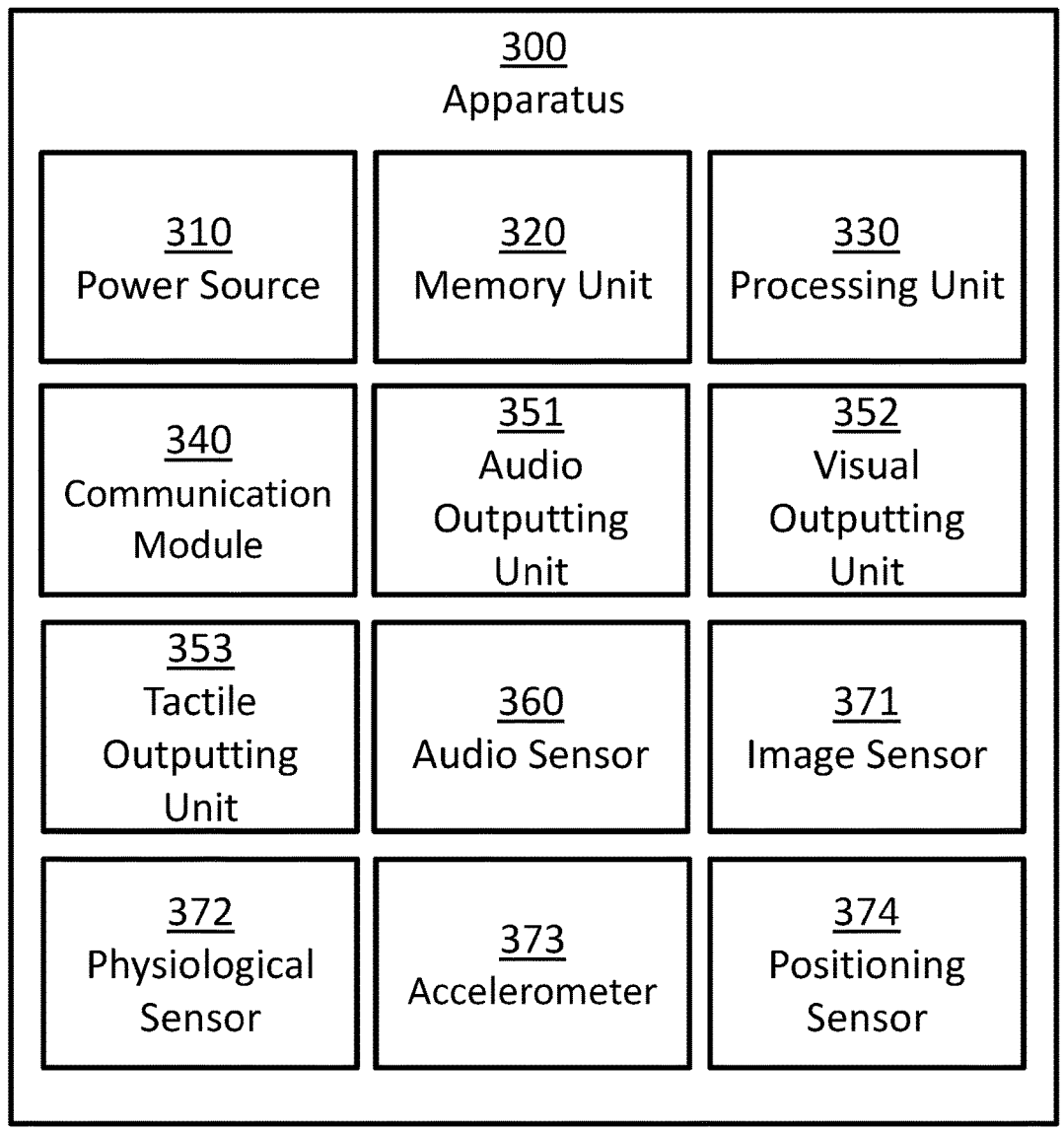

In some embodiments, possible implementations of wearable apparatuses 121, 122, 123, 124, 125, and/or 126 may include apparatus 300, for example as described in FIGS. 3A and 3B. In some embodiments, apparatus 300 may comprise two or more separate parts. For example, apparatus 300 may comprise parts 121, 122, 123, 124, 125, and/or 126. In some examples, the separate parts may communicate by wires and/or wirelessly.

Figure 2A:
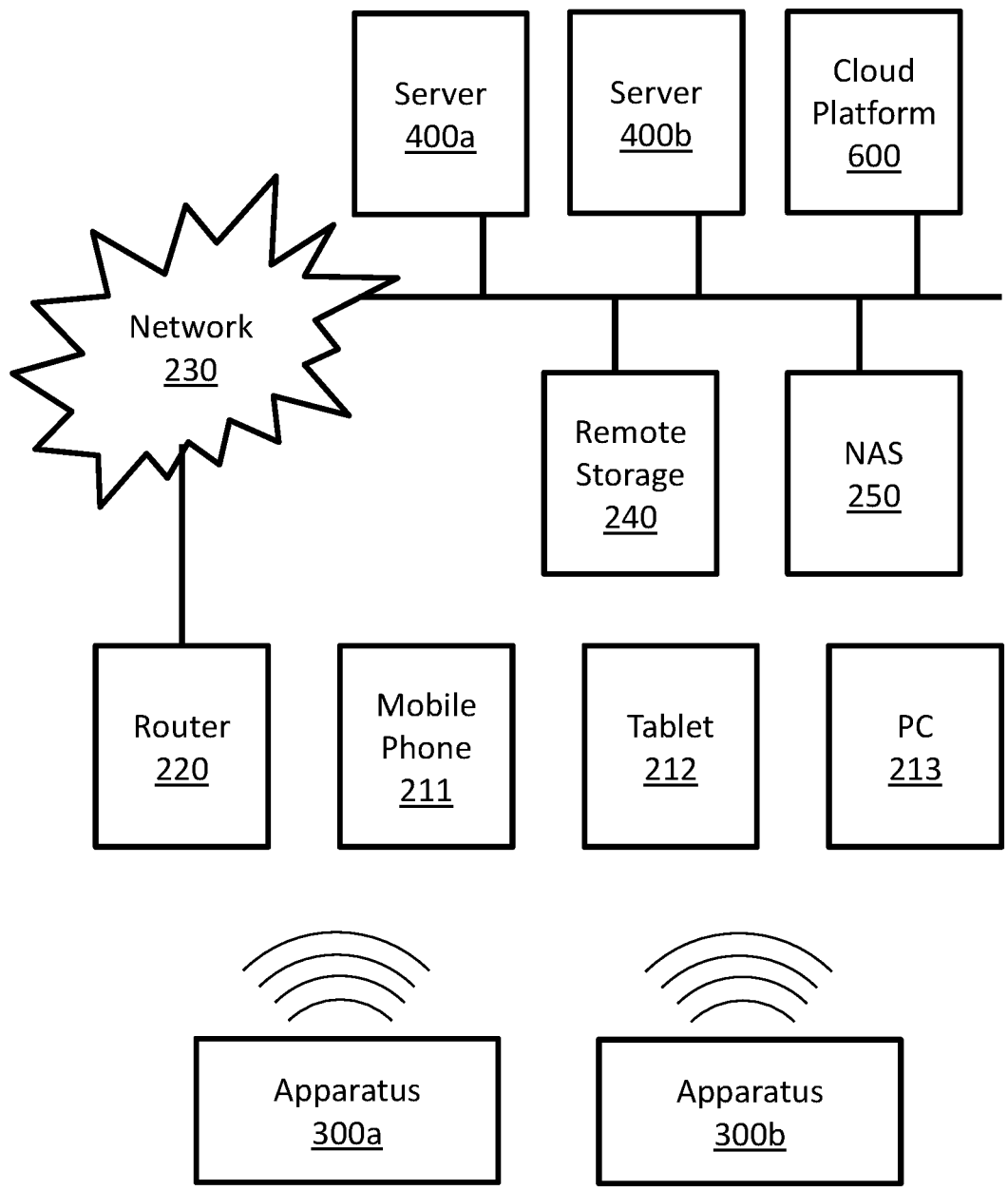
FIGS. 2A and 2B are block diagrams illustrating some possible implementation of a communication system.

FIG. 2A is a block diagram illustrating a possible implementation of a communicating system. In this example, apparatuses 300a and 300b may communicate with server 400a, with server 400b, with cloud platform 500, with each other, and so forth. Some possible implementations of apparatuses 300a and 300b may include apparatus 300, for example as described in FIGS. 3A and 3B. Some possible implementations of servers 400a and/or 400b may include server 400, for example as described in FIG. 4. Some possible implementations of cloud platform 500 are described in FIGS. 5A, 5B and 5C. In this example, apparatus 300a and/or apparatus 300b may communicate directly with mobile phone 211, tablet 212, and/or personal computer (PC) 213. Apparatus 300a and/or apparatus 300b may communicate with local router 220 directly, and/or through at least one of mobile phone 211, tablet 212, and/or personal computer (PC) 213. In this example, local router 220 may be connected to communication network 230. Some examples of communication network 230 may include the Internet, phone networks, cellular networks, satellite communication networks, private communication networks, virtual private networks (VPN), and so forth. Apparatus 300a and/or apparatus 300b may connect to communication network 230 through local router 220 and/or directly. Apparatus 300a and/or apparatus 300b may communicate with other devices, such as servers 400a, server 400b, cloud platform 500, remote storage 240 and network attached storage (NAS) 250, and so forth, through communication network 230 and/or directly.

Figure 2B:
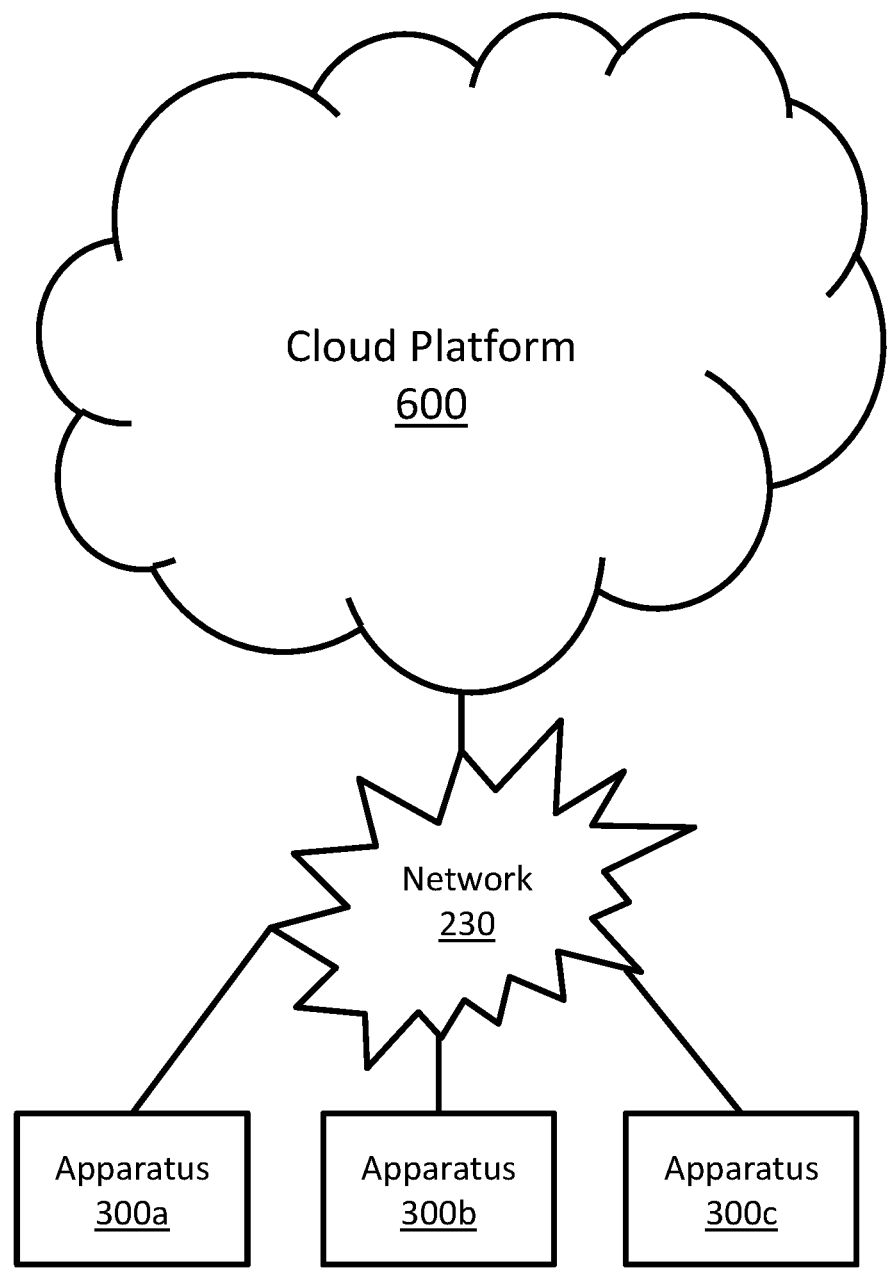

FIG. 2B is a block diagram illustrating a possible implementation of a communicating system. In this example, apparatus 300a, apparatus 300b and/or apparatus 300c may communicate with cloud platform 500 and/or with each other through communication network 230. Possible implementations of apparatuses 300a, 300b and 300c may include apparatus 300, for example as described in FIGS. 3A and 3B. Some possible implementations of cloud platform 500 are described in FIGS. 5A, 5B and 5C. Some examples of communication network 230 may include the Internet, phone networks, cellular networks, satellite communication networks, private communication networks, virtual private networks (VPN), and so forth.

FIGS. 2A and 2B illustrate some possible implementations of a communication system. In some embodiments, other communication systems that enable communication between apparatus 300 and server 400 may be used. In some embodiments, other communication systems that enable communication between apparatus 300 and cloud platform 500 may be used. In some embodiments, other communication systems that enable communication among a plurality of apparatuses 300 may be used.

FIG. 3A is a block diagram illustrating a possible implementation of apparatus 300. In this example, apparatus 300 comprises: one or more power sources 310; one or more memory units 320; one or more processing units 330; and one or more audio sensors 360. In some implementations additional components may be included in apparatus 300, while some components listed above may be excluded. In some embodiments, power sources 310 and/or audio sensors 360 may be excluded from the implementation of apparatus 300. In some embodiments, apparatus 300 may further comprise one or more of the followings: one or more communication modules 340; one or more audio output units 351; one or more visual outputting units 352; one or more tactile outputting units 353; one or more image sensors 371; one or more physiological sensors 372; one or more accelerometers 373; one or more positioning sensors 374; one or more chemical sensors; one or more temperature sensors; one or more barometers; one or more environmental sensors; one or more pressure sensors; one or more proximity sensors; one or more electrical impedance sensors; one or more electrical voltage sensors; one or more electrical current sensors; one or more clocks; one or more user input devices; one or more keyboards; one or more mouses; one or more touch pads; one or more touch screens; one or more antennas; one or more output devices; one or more audio speakers; one or more display screens; one or more augmented reality display systems; one or more LED indicators; and so forth.

FIG. 3B is a block diagram illustrating a possible implementation of apparatus 300. In this example, apparatus 300 comprises: one or more power sources 310; one or more memory units 320; one or more processing units 330; one or more communication modules 340; one or more audio output units 351; one or more visual outputting units 352; one or more tactile outputting units 353; one or more audio sensors 360; one or more image sensors 371; one or more physiological sensors 372; one or more accelerometers 373; and one or more positioning sensors 374. In some implementations additional components may be included in apparatus 300, while some components listed above may be excluded. In some embodiments, one or more of the followings may be excluded from the implementation of apparatus 300: power sources 310; communication modules 340; audio output units 351; visual outputting units 352; tactile outputting units 353; audio sensors 360; image sensors 371; physiological sensors 372; accelerometers 373; and positioning sensors 374. In some embodiments, apparatus 300 may further comprise one or more of the followings: one or more chemical sensors; one or more temperature sensors; one or more barometers; one or more environmental sensors; one or more pressure sensors; one or more proximity sensors; one or more electrical impedance sensors; one or more electrical voltage sensors; one or more electrical current sensors; one or more clocks; one or more user input devices; one or more keyboards; one or more mouses; one or more touch pads; one or more touch screens; one or more antennas; one or more output devices; one or more audio speakers; one or more display screens; one or more augmented reality display systems; one or more LED indicators; and so forth.

In some embodiments, the one or more power sources 310 may be configured to: power apparatus 300; power server 400; power cloud platform 500; power computational node 510; and so forth. Some possible implementation examples the one or more power sources 310 may comprise: one or more electric batteries; one or more capacitors; one or more connections to external power sources; one or more power convertors; one or more electric power generators; any combination of the above; and so forth.

In some embodiments, the one or more processing units 330 may be configured to execute software programs, for example software programs stored in the one or more memory units 320, software programs received through the one or more communication modules 340, and so forth. Some possible implementation examples of processing units 330 may comprise: one or more single core processors; one or more multicore processors; one or more controllers; one or more application processors; one or more system on a chip processors; one or more central processing units; one or more graphical processing units; one or more neural processing units; any combination of the above; and so forth. In some examples, the executed software programs may store information in memory units 320. In some cases, the executed software programs may retrieve information from memory units 320.

In some embodiments, the one or more communication modules 340 may be configured to receive and/or transmit information. Some possible implementation examples of communication modules 340 may comprise: wired communication devices; wireless communication devices; optical communication devices; electrical communication devices; radio communication devices; sonic and/or ultrasonic communication devices; electromagnetic induction communication devices; infrared communication devices; transmitters; receivers; transmitting and receiving devices; modems; network interfaces; wireless USB communication devices, wireless LAN communication devices; Wi-Fi communication devices; LAN communication devices; USB communication devices; firewire communication devices; bluetooth communication devices; cellular communication devices, such as GSM, CDMA, GPRS, W-CDMA, EDGE, CDMA2000, etc.; satellite communication devices; and so forth.

In some implementations, control signals and/or synchronization signals may be transmitted and/or received through communication modules 340. In some implementations, information received though communication modules 340 may be stored in memory units 320. In some implementations, information retrieved from memory units 320 may be transmitted using communication modules 340. In some implementations, input and/or user input may be transmitted and/or received through communication modules 340. In some implementations, audio data may be transmitted and/or received through communication modules 340, such as audio data captured using audio sensors 360. In some implementations, visual data, such as images and/or videos, may be transmitted and/or received through communication modules 340, such as images and/or videos captured using image sensors 371. In some implementations, physiological data may be transmitted and/or received through communication modules 340, such as physiological data captured using physiological sensors 372. In some implementations, proper acceleration information may be transmitted and/or received through communication modules 340, such as proper acceleration information captured using accelerometers 373. In some implementations, positioning information may be transmitted and/or received through communication modules 340, such as positioning information captured using positioning sensors 374.

In some implementations, output information may be transmitted and/or received through communication modules 340. In some implementations, audio output information may be transmitted and/or received through communication modules 340. For example, audio output information to be outputted using audio outputting units 351 may be received through communication modules 340. In some implementations, visual output information may be transmitted and/or received through communication modules 340. For example, visual output information to be outputted using visual outputting units 352 may be received through communication modules 340. In some implementations, tactile output information may be transmitted and/or received through communication modules 340. For example, tactile output information to be outputted using tactile outputting units 353 may be received through communication modules 340.

In some embodiments, the one or more audio outputting units 351 may be configured to output audio to a user, for example through a headset, through one or more audio speakers, and so forth. In some embodiments, the one or more visual outputting units 352 may be configured to output visual information to a user, for example through a display screen, through an augmented reality display system, through a printer, through LED indicators, and so forth. In some embodiments, the one or more tactile outputting units 353 may be configured to output tactile feedbacks to a user, for example through vibrations, through motions, by applying forces, and so forth. In some examples, output may be provided: in real time; offline; automatically; periodically; upon request; and so forth. In some examples, apparatus 300 may be a wearable apparatus and the output may be provided to: a wearer of the wearable apparatus; a caregiver of the wearer of the wearable apparatus; and so forth. In some examples, the output may be provided to: a caregiver; clinicians; insurers; and so forth.

In some embodiments, the one or more audio sensors 360 may be configured to capture audio data. Some possible examples of audio sensors 360 may include: connectors to microphones; microphones; unidirectional microphones; bidirectional microphones; cardioid microphones; omnidirectional microphones; onboard microphones; wired microphones; wireless microphones; any combination of the above; and so forth. In some cases, audio data captured using audio sensors 360 may be stored in memory, for example in memory units 320. In some cases, audio data captured using audio sensors 360 may be transmitted, for example using communication device 340 to an external system, such as server 400, cloud platform 500, computational node 510, apparatus 300, and so forth. In some cases, audio data captured using audio sensors 360 may be processed, for example using processing units 330. For example, the audio data captured using audio sensors 360 may be: compressed; preprocessed using filters, such as low pass filters, high pass filters, etc.; downsampled; and so forth. In some cases, audio data captured using audio sensors 360 may be analyzed, for example using processing units 330. For example, audio data captured using audio sensors 360 may be analyzed to identify low level features, speakers, speech, audio triggers, and so forth. In another example, audio data captured using audio sensors 360 may be applied to an inference model.

In some embodiments, the one or more image sensors 371 may be configured to capture visual data. Some possible examples of image sensors 371 may include: CCD sensors; CMOS sensors; stills image sensors; video image sensors; 2D image sensors; 3D image sensors; and so forth. Some possible examples of visual data may include: still images; video clips; continuous video; 2D images; 2D videos; 3D images; 3D videos; microwave images; terahertz images; ultraviolet images; infrared images; x-ray images; gamma ray images; visible light images; microwave videos; terahertz videos; ultraviolet videos; infrared videos; visible light videos; x-ray videos; gamma ray videos; and so forth. In some cases, visual data captured using image sensors 371 may be stored in memory, for example in memory units 320. In some cases, visual data captured using image sensors 371 may be transmitted, for example using communication device 340 to an external system, such as server 400, cloud platform 500, computational node 510, apparatus 300, and so forth. In some cases, visual data captured using image sensors 371 may be processed, for example using processing units 330. For example, the visual data captured using image sensors 371 may be: compressed; preprocessed using filters, such as low pass filter, high pass filter, etc.; downsampled; and so forth. In some cases, visual data captured using image sensors 371 may be analyzed, for example using processing units 330. For example, visual data captured using image sensors 371 may be analyzed to identify one or more of: low level visual features; objects; faces; persons; events; visual triggers; and so forth. In another example, visual data captured using image sensors 371 may be applied to an inference model.

In some embodiments, the one or more physiological sensors 372 may be configured to capture physiological data. Some possible examples of physiological sensors 372 may include: glucose sensors; electrocardiogram sensors; electroencephalogram sensors; electromyography sensors; odor sensors; respiration sensors; blood pressure sensors; pulse oximeter sensors; heart rate sensors; perspiration sensors; and so forth. In some cases, physiological data captured using physiological sensors 372 may be stored in memory, for example in memory units 320. In some cases, physiological data captured using physiological sensors 372 may be transmitted, for example using communication device 340 to an external system, such as server 400, cloud platform 500, computational node 510, apparatus 300, and so forth. In some cases, physiological data captured using physiological sensors 372 may be processed, for example using processing units 330. For example, the physiological data captured using physiological sensors 372 may be compressed, downsampled, and so forth. In some cases, physiological data captured using physiological sensors 372 may be analyzed, for example using processing units 330. For example, physiological data captured using physiological sensors 372 may be analyzed to identify events, triggers, and so forth. In another example, physiological data captured using physiological sensors 372 may be applied to an inference model.

In some embodiments, the one or more accelerometers 373 may be configured to capture proper acceleration information, for example by: measuring proper acceleration of apparatus 300; detecting changes in proper acceleration of apparatus 300; and so forth. In some embodiments, the one or more accelerometers 373 may comprise one or more gyroscopes. In some cases, information captured using accelerometers 373 may be stored in memory, for example in memory units 320. In some cases, information captured using accelerometers 373 may be transmitted, for example using communication device 340 to an external system, such as server 400, cloud platform 500, computational node 510, apparatus 300, and so forth. In some cases, information captured using accelerometers 373 may be processed, for example using processing units 330. For example, the information captured using accelerometers 373 may be compressed, downsampled, and so forth. In some cases, information captured using accelerometers 373 may be analyzed, for example using processing units 330. For example, the information captured using accelerometers 373 may be analyzed to identify events, triggers, and so forth. In another example, the information captured using accelerometers 373 may be applied to an inference model.

In some embodiments, the one or more positioning sensors 374 may be configured to: obtain positioning information associated with apparatus 300; detect changes in the position of apparatus 300; and so forth. In some embodiments, the positioning sensors 374 may be implemented using different technologies, such as: Global Positioning System (GPS); GLObal NAvigation Satellite System (GLONASS); Galileo global navigation system, BeiDou navigation system; other Global Navigation Satellite Systems (GNSS); Indian Regional Navigation Satellite System (IRNSS); Local Positioning Systems (LPS), Real-Time Location Systems (RTLS); Indoor Positioning System (IPS); Wi-Fi based positioning systems; cellular triangulation; and so forth. In some embodiments, the one or more positioning sensors 374 may comprise one or more altimeters, and be configured to measure altitude and/or to detect changes in altitude. In some embodiments, information captured using positioning sensors 374 may be stored in memory, for example in memory units 320. In some cases, information captured using positioning sensors 374 may be transmitted, for example using communication device 340 to an external system, such as server 400, cloud platform 500, computational node 510, apparatus 300, and so forth. In some cases, information captured using positioning sensors 374 may be processed, for example using processing units 330. For example, the information captured using positioning sensors 374 may be compressed, downsampled, and so forth. In some cases, information captured using positioning sensors 374 may be analyzed, for example using processing units 330. For example, the information captured using positioning sensors 374 may be analyzed to identify events, triggers, and so forth. In another example, the information captured using positioning sensors 374 may be applied to an inference model.

Figure 4:
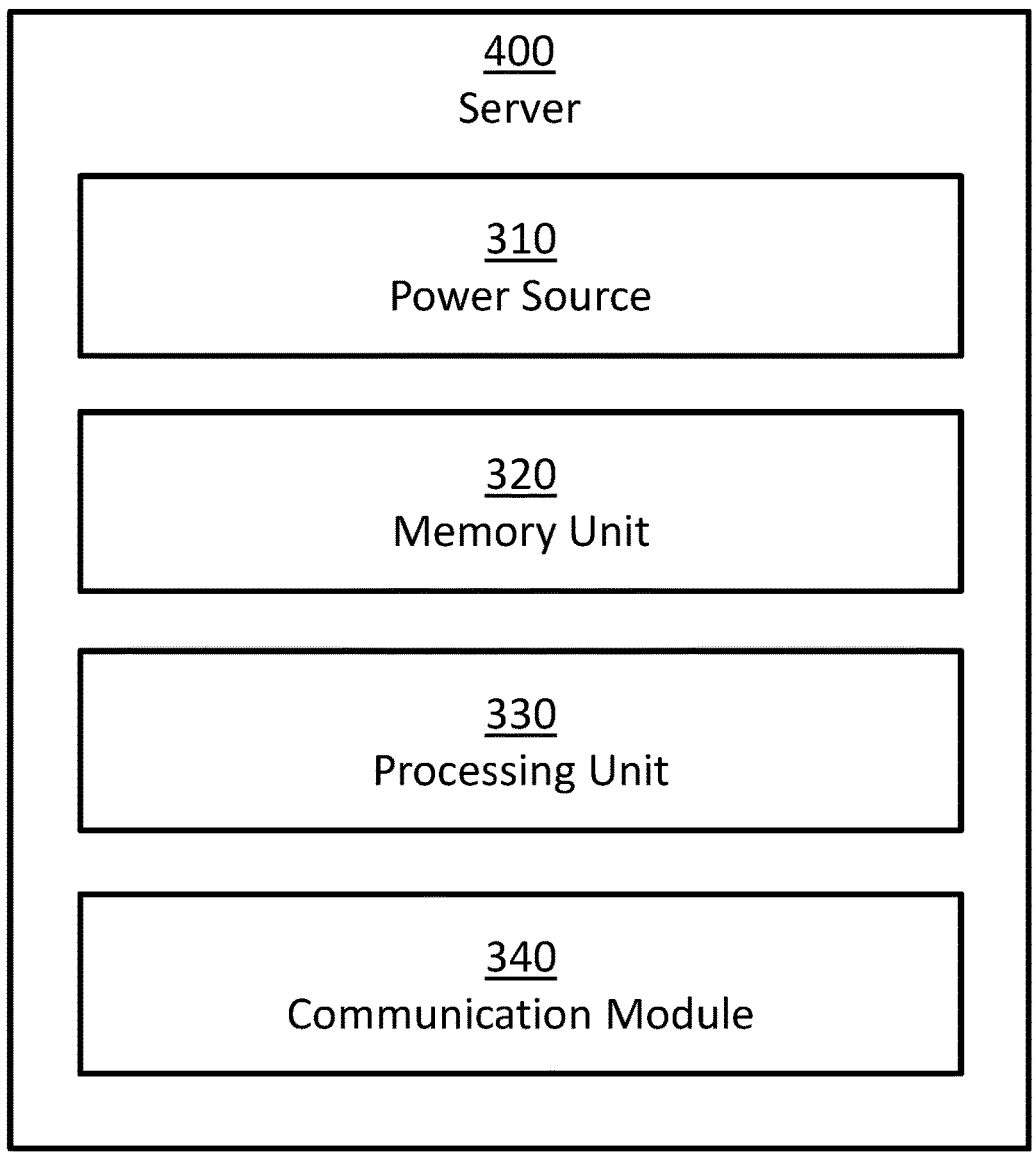
FIG. 4 is a block diagram illustrating a possible implementation of a server.

FIG. 4 is a block diagram illustrating a possible implementation of a server 400. In this example, server 400 comprises: one or more power sources 310; one or more memory units 320; one or more processing units 330; and one or more communication modules 340. In some implementations additional components may be included in server 400, while some components listed above may be excluded. In some embodiments, power sources 310 and/or communication modules 340 may be excluded from the implementation of server 400. In some embodiments, server 400 may further comprise one or more of the followings: one or more audio output units 351; one or more visual outputting units 352; one or more tactile outputting units 353; one or more audio sensors 360; one or more image sensors 371; one or more accelerometers 373; one or more positioning sensors 374; one or more chemical sensors; one or more temperature sensors; one or more barometers; one or more environmental sensors; one or more pressure sensors; one or more proximity sensors; one or more electrical impedance sensors; one or more electrical voltage sensors; one or more electrical current sensors; one or more clocks; one or more user input devices; one or more keyboards; one or more mouses; one or more touch pads; one or more touch screens; one or more antennas; one or more output devices; one or more audio speakers; one or more display screens; one or more augmented reality display systems; one or more LED indicators; and so forth.

Figure 5A:
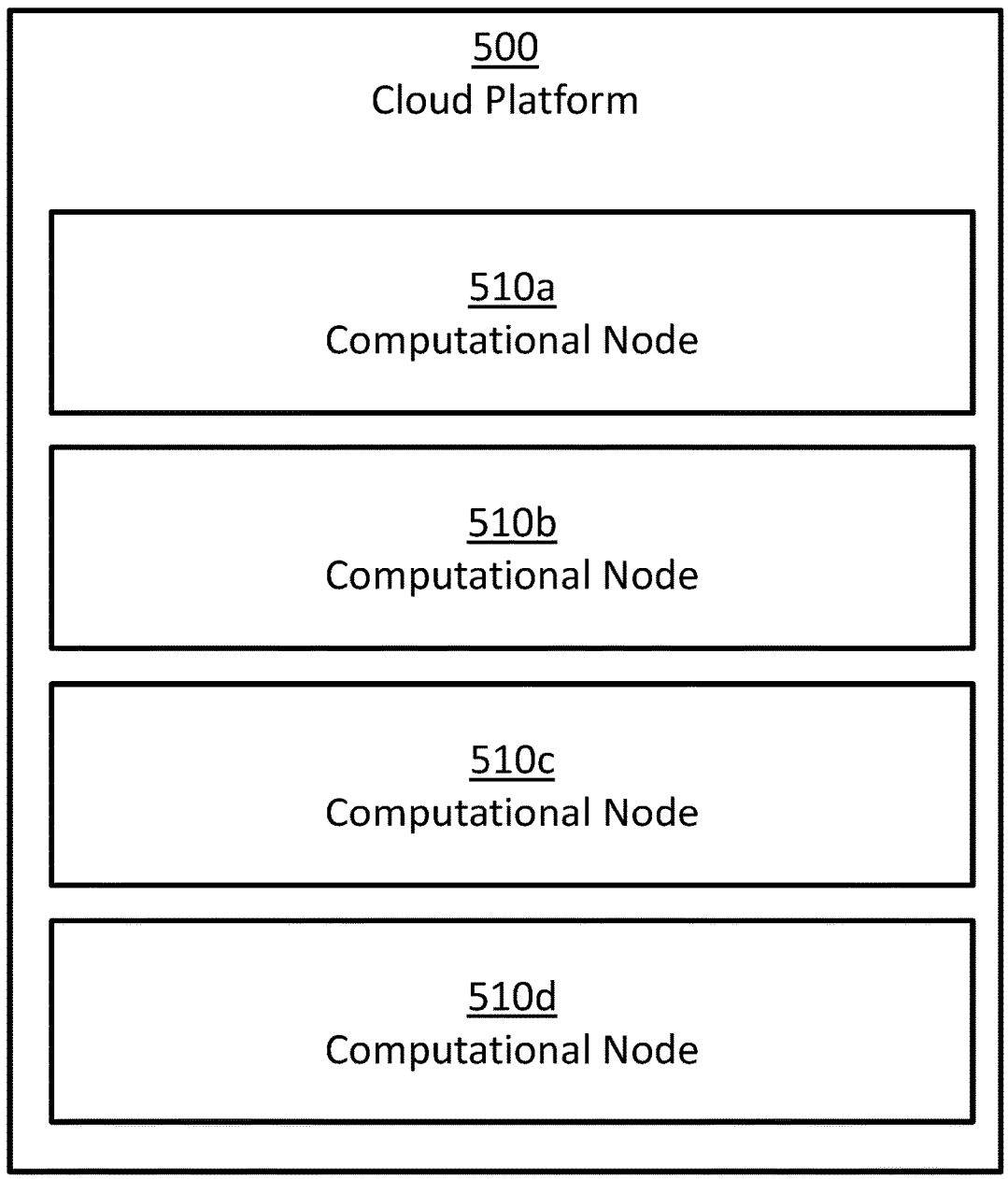
FIGS. 5A and 5B are block diagrams illustrating some possible implementation of a cloud platform.

FIG. 5A is a block diagram illustrating a possible implementation of cloud platform 500. In some examples, cloud platform 500 may comprise a number of computational nodes, in this example four computational nodes: computational node 510*a*, computational node 510*b*, computational node 510*c* and computational node 510*d*. In some examples, a possible implementation of computational nodes 510a, 510b, 510c and/or 510d may comprise server 400 as described in FIG. 4. In some examples, a possible implementation of computational nodes 510a, 510b, 510c and/or 510d may comprise computational node 510 as described in FIG. 5C.

Figure 5B:
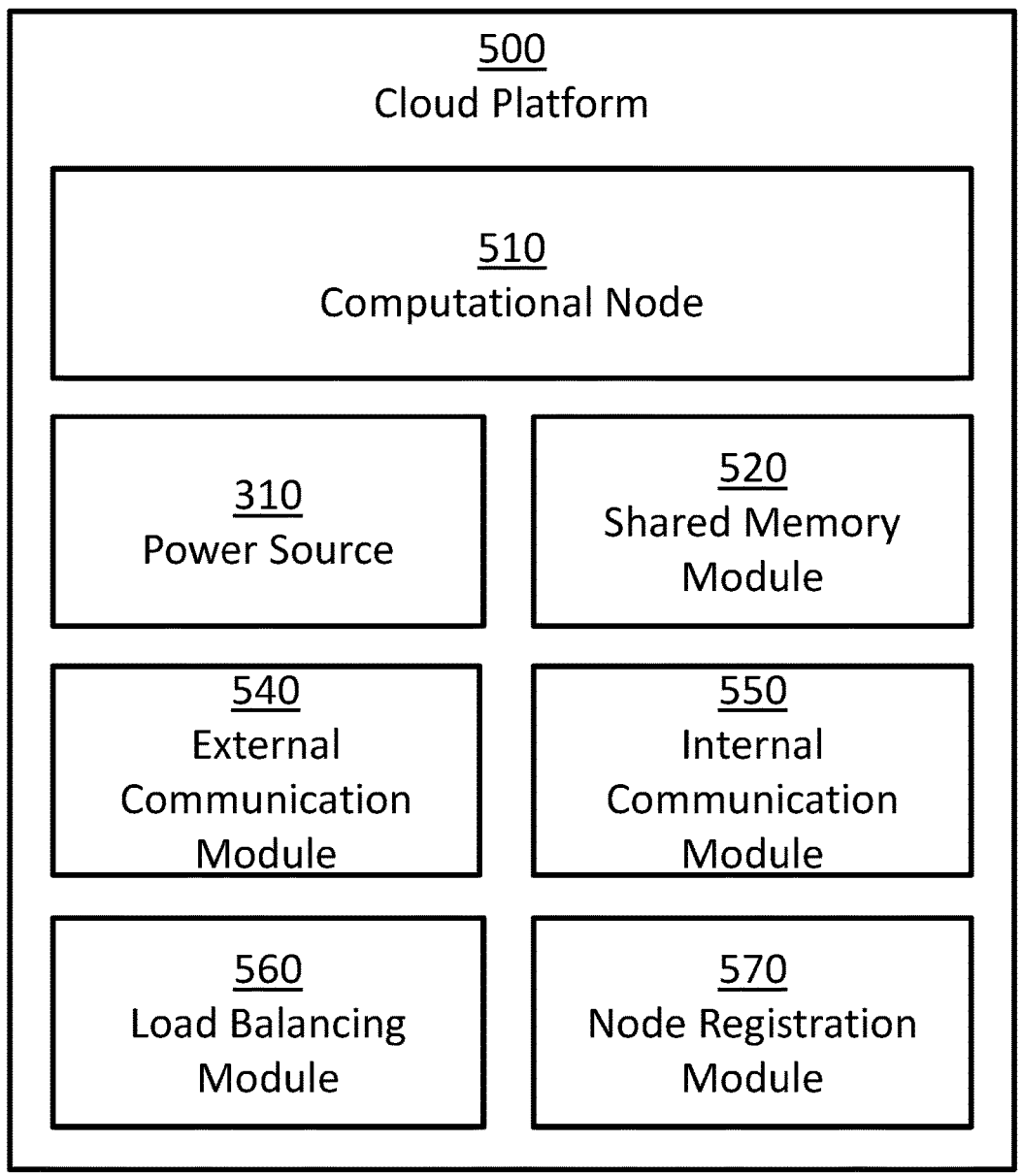

FIG. 5B is a block diagram illustrating a possible implementation of cloud platform 500. In this example, cloud platform 500 comprises: one or more computational nodes 510; one or more power sources 310; one or more shared memory modules 520; one or more external communication modules 540; one or more internal communication modules 550; one or more load balancing modules 560; and one or more node registration modules 570. In some implementations additional components may be included in cloud platform 500, while some components listed above may be excluded. In some embodiments, one or more of the followings may be excluded from the implementation of cloud platform 500: power sources 310; shared memory modules 520; external communication modules 540; internal communication modules 550; load balancing modules 560; and node registration modules 570. In some embodiments, cloud platform 500 may further comprise one or more of the followings: one or more audio output units 351; one or more visual outputting units 352; one or more tactile outputting units 353; one or more audio sensors 360; one or more image sensors 371; one or more accelerometers 373; one or more positioning sensors 374; one or more chemical sensors; one or more temperature sensors; one or more barometers; one or more environmental sensors; one or more pressure sensors; one or more proximity sensors; one or more electrical impedance sensors; one or more electrical voltage sensors; one or more electrical current sensors; one or more clocks; one or more user input devices; one or more keyboards; one or more mouses; one or more touch pads; one or more touch screens; one or more antennas; one or more output devices; one or more audio speakers; one or more display screens; one or more augmented reality display systems; one or more LED indicators; and so forth.

Figure 5C:
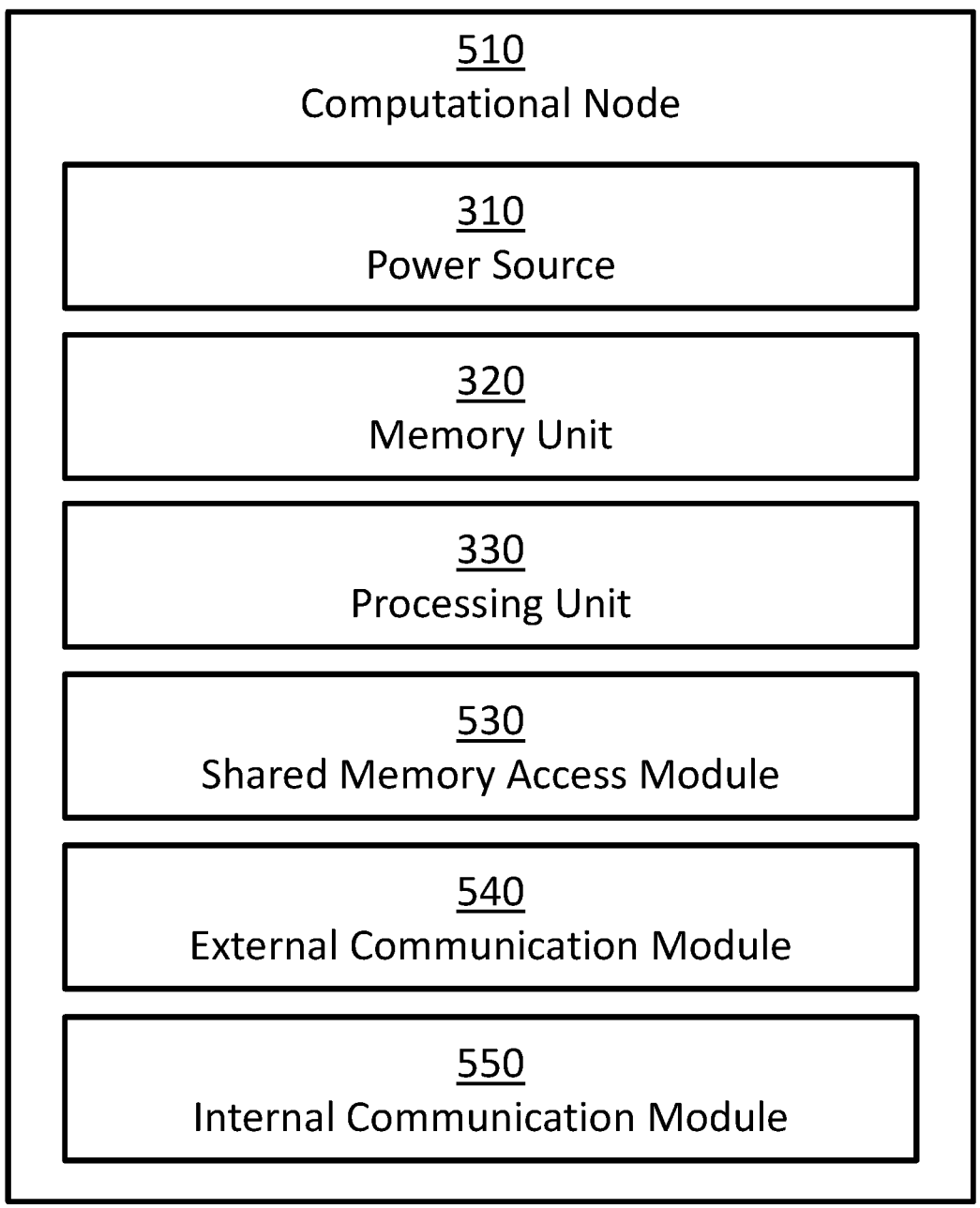
FIG. 5C is a block diagram illustrating a possible implementation of a computational node.

FIG. 5C is a block diagram illustrating a possible implementation of computational node 510 of a cloud platform, such as cloud platform 500. In this example computational node 510 comprises: one or more power sources 310; one or more memory units 320; one or more processing units 330; one or more shared memory access modules 530; one or more external communication modules 540; and one or more internal communication modules 550. In some implementations additional components may be included in computational node 510, while some components listed above may be excluded. In some embodiments, one or more of the followings may be excluded from the implementation of computational node 510: power sources 310; memory units 320; shared memory access modules 530; external communication modules 540; and internal communication modules 550. In some embodiments, computational node 510 may further comprise one or more of the followings: one or more audio output units 351; one or more visual outputting units 352; one or more tactile outputting units 353; one or more audio sensors 360; one or more image sensors 371; one or more accelerometers 373; one or more positioning sensors 374; one or more chemical sensors; one or more temperature sensors; one or more barometers; one or more environmental sensors; one or more pressure sensors; one or more proximity sensors; one or more electrical impedance sensors; one or more electrical voltage sensors; one or more electrical current sensors; one or more clocks; one or more user input devices; one or more keyboards; one or more mouses; one or more touch pads; one or more touch screens; one or more antennas; one or more output devices; one or more audio speakers; one or more display screens; one or more augmented reality display systems; one or more LED indicators; and so forth.

In some embodiments, external communication modules 540 and internal communication modules 550 may be implemented as a combined communication module, for example as communication modules 340. In some embodiments, one possible implementation of cloud platform 500 may comprise server 400. In some embodiments, one possible implementation of computational node 510 may comprise server 400. In some embodiments, one possible implementation of shared memory access modules 530 may comprise the usage of internal communication modules 550 to send information to shared memory modules 520 and/or receive information from shared memory modules 520. In some embodiments, node registration modules 570 and load balancing modules 560 may be implemented as a combined module.

In some embodiments, the one or more shared memory modules 520 may be accessed by more than one computational node. Therefore, shared memory modules 520 may allow information sharing among two or more computational nodes 510. In some embodiments, the one or more shared memory access modules 530 may be configured to enable access of computational nodes 510 and/or the one or more processing units 330 of computational nodes 510 to shared memory modules 520. In some examples, computational nodes 510 and/or the one or more processing units 330 of computational nodes 510, may access shared memory modules 520, for example using shared memory access modules 530, in order to perform one or more of: executing software programs stored on shared memory modules 520; store information in shared memory modules 520; retrieve information from the shared memory modules 520; and so forth.

In some embodiments, the one or more internal communication modules 550 may be configured to receive information from one or more components of cloud platform 500, and/or to transmit information to one or more components of cloud platform 500. For example, control signals and/or synchronization signals may be sent and/or received through internal communication modules 550. In another example, input information for computer programs, output information of computer programs, and/or intermediate information of computer programs, may be sent and/or received through internal communication modules 550. In another example, information received though internal communication modules 550 may be stored in memory units 320, in shared memory units 520, and so forth. In an additional example, information retrieved from memory units 320 and/or shared memory units 520 may be transmitted using internal communication modules 550. In another example, user input data may be transmitted and/or received using internal communication modules 550.

In some embodiments, the one or more external communication modules 540 may be configured to receive and/or to transmit information. For example, control signals and/or synchronization signals may be sent and/or received through external communication modules 540. In another example, information received though external communication modules 540 may be stored in memory units 320, in shared memory units 520, and so forth. In an additional example, information retrieved from memory units 320 and/or shared memory units 520 may be transmitted using external communication modules 540. In another example, input data may be transmitted and/or received using external communication modules 540. Examples of such input data may include: input data inputted by a user using user input devices; information captured from the environment of apparatus 300 using one or more sensors; and so forth. Examples of such sensors may include: audio sensors 360; image sensors 371; physiological sensors 372; accelerometers 373; and positioning sensors 374; chemical sensors; temperature sensors; barometers; environmental sensors; pressure sensors; proximity sensors; electrical impedance sensors; electrical voltage sensors; electrical current sensors; and so forth.

In some embodiments, the one or more node registration modules 570 may be configured to track the availability of the computational nodes 510. In some examples, node registration modules 570 may be implemented as: a software program, such as a software program executed by one or more of the computational nodes 510; a hardware solution; a combined software and hardware solution; and so forth. In some implementations, node registration modules 570 may communicate with computational nodes 510, for example using internal communication modules 550. In some examples, computational nodes 510 may notify node registration modules 570 of their status, for example by sending messages: at computational node 510 startups; at computational node 510 shutdowns; at periodic times; at selected times; in response to queries received from node registration modules 570; and so forth. In some examples, node registration modules 570 may query about computational nodes 510 status, for example by sending messages: at node registration module 570 startup; at periodic times; at selected times; and so forth.

In some embodiments, the one or more load balancing modules 560 may be configured to divide the work load among computational nodes 510. In some examples, load balancing modules 560 may be implemented as: a software program, such as a software program executed by one or more of the computational nodes 510; a hardware solution; a combined software and hardware solution; and so forth. In some implementations, load balancing modules 560 may interact with node registration modules 570 in order to obtain information regarding the availability of the computational nodes 510. In some implementations, load balancing modules 560 may communicate with computational nodes 510, for example using internal communication modules 550. In some examples, computational nodes 510 may notify load balancing modules 560 of their status, for example by sending messages: at computational node 510 startups; at computational node 510 shutdowns; at periodic times; at selected times; in response to queries received from load balancing modules 560; and so forth. In some examples, load balancing modules 560 may query about computational nodes 510 status, for example by sending messages: at load balancing module 560 startup; at periodic times; at selected times; and so forth.

Figure 6A:
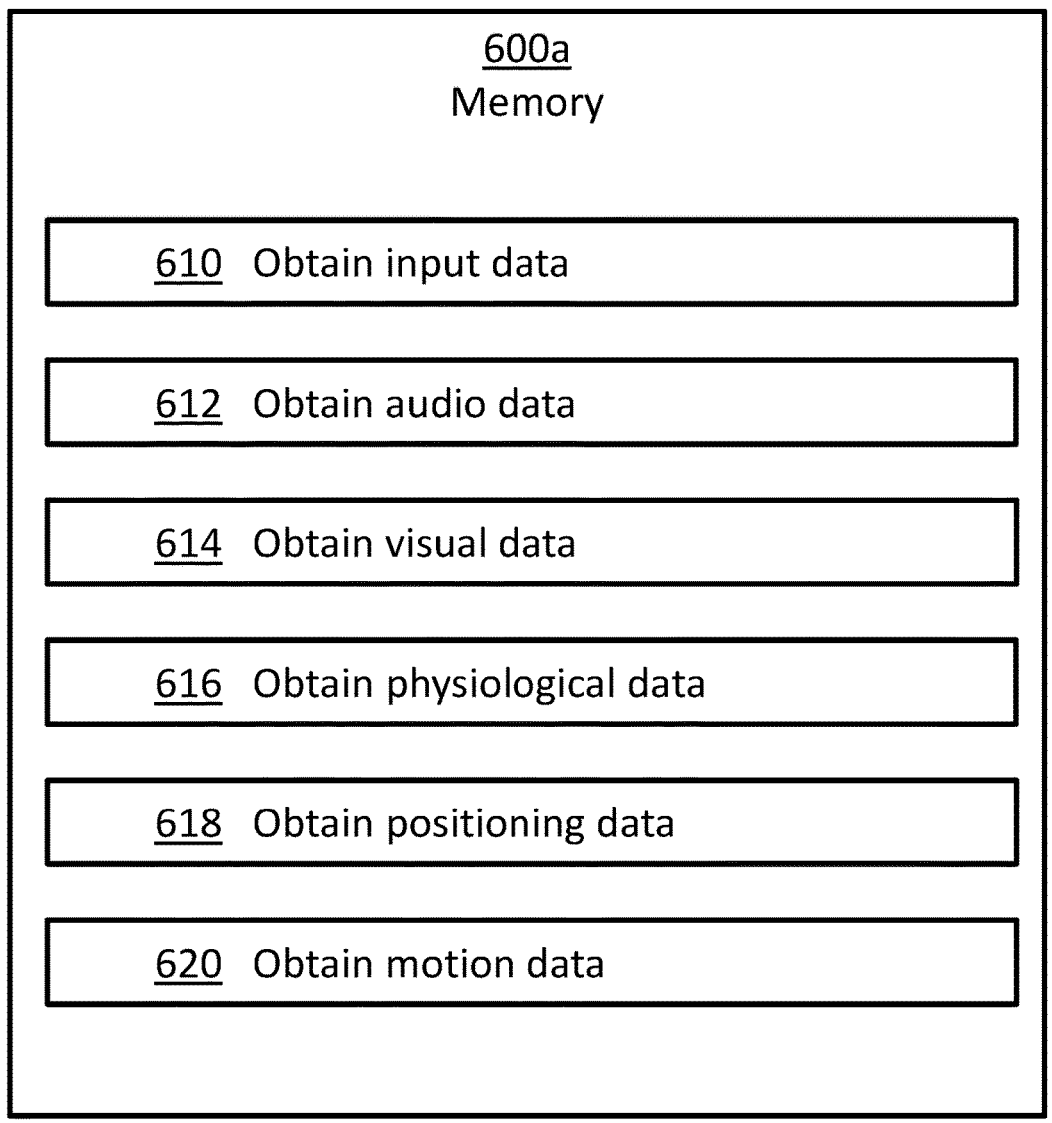
FIGS. 6A and 6B illustrate exemplary embodiments of memory containing software modules.
Figure 6B:
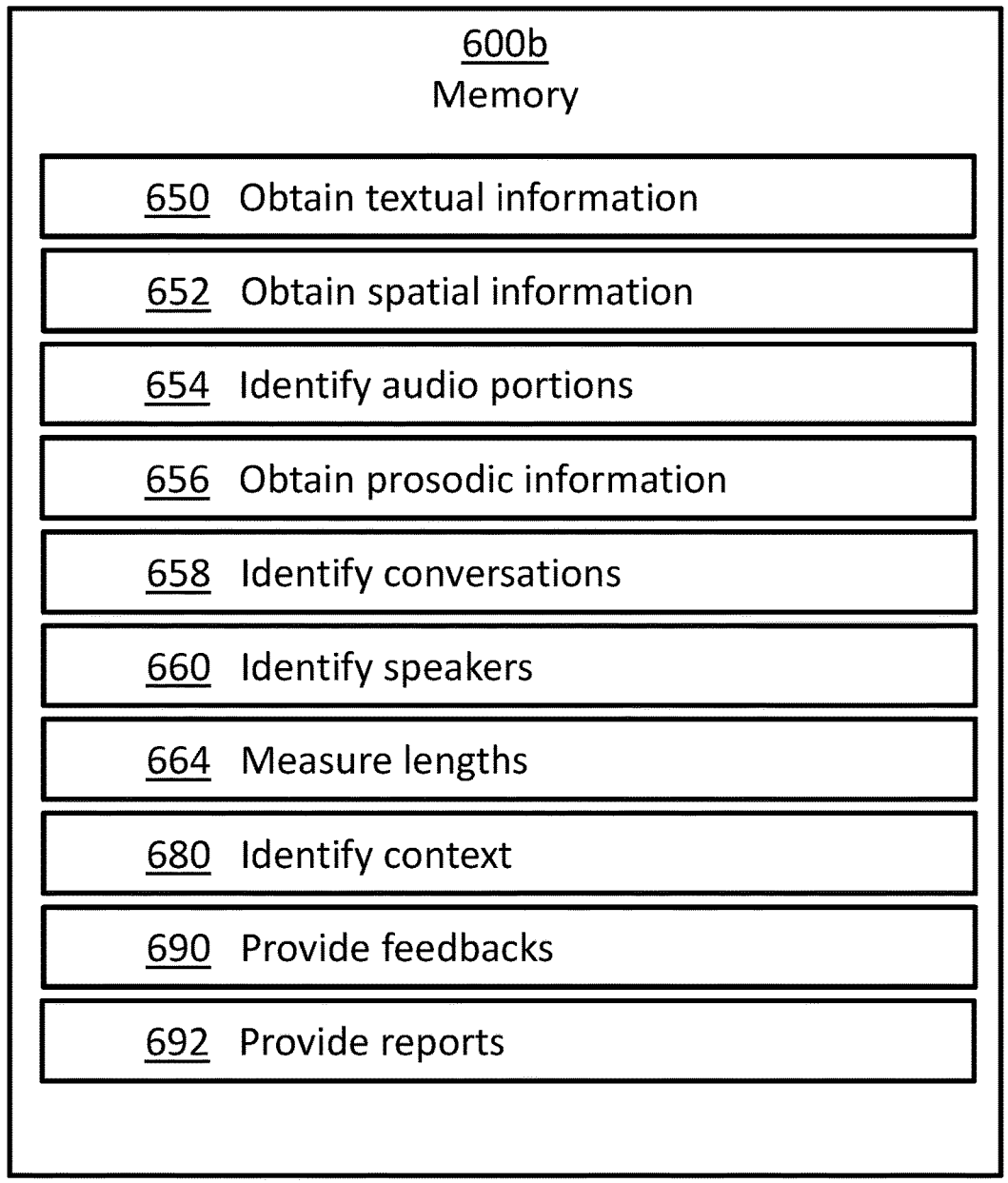

FIG. 6A illustrates an exemplary embodiment of memory 600a containing software modules, and FIG. 6B illustrates an exemplary embodiment of memory 600b containing software modules. In some examples, memory 600a may be separate and/or integrated with memory 600b. In addition, memory 600a and memory 600b may be separate from and/or integrated with memory units 320, separate from and/or integrated with shared memory modules 520, and so forth. In some examples, memory 600a and/or memory 600b may be included in a single device, such as apparatus 300, in server 400, in cloud platform 500, in computational node 510, and so forth. In some examples, at least one of memory 600a and memory 600b may be distributed across several devices, such as one or more apparatuses 300, one or more servers 400, one or more cloud platforms 500, one or more computational nodes 510, and so forth. Memory 600a and memory 600b may store more or fewer modules than those shown in FIGS. 6A and 6B. In this example, memory 600a may comprise: module for obtaining input data (610), module for obtaining audio data (612), module for obtaining visual data (614), module for obtaining physiological data (616), module for obtaining positioning data (618), and module for obtaining motion data (620). In this example, memory 600b may comprise: module for obtaining textual information (650), module for obtaining spatial information (652), module for identifying audio portions (654), module for obtaining prosodic information (656), module for identifying conversations (658), module for identifying speakers (660), module for measuring lengths (664), module for identifying context (680), module for providing feedbacks (690), and module for providing reports (692). The above modules may be implemented in software, hardware, firmware, a mix of any of those, or the like. For example, if the modules are implemented in software, they may contain software instructions for execution by at least one processing device, such as processing unit 330, by apparatus 300, by server 400, by cloud platform 500, by computational node 510, and so forth.

In some embodiments, obtaining input data (610) may comprise one or more of: obtaining audio data and/or preprocessed audio data, for example using module 612 for obtaining audio data; obtaining visual data and/or preprocessed visual data, for example using module 614 for obtaining visual data; obtaining physiological data and/or preprocessed physiological data, for example using module 616 for obtaining physiological data; obtaining positioning data and/or preprocessed positioning data, for example using module 618 for obtaining positioning data; obtaining motion data and/or preprocessed motion data, for example using module 620 for obtaining motion data; and so forth. In some embodiments, a user may wear a wearable apparatus comprising one or more sensors, such as a wearable version of apparatus 300, and obtaining input data (610) may comprise obtaining input data captured from the environment of the user using the input sensors.

In some embodiments, obtaining audio data (612) may comprise obtaining and/or capturing audio data from one or more audio sensors, for example using audio sensors 360. In some examples, the one or more audio sensors may comprise one or more wearable audio sensors, such as a wearable version of audio sensors 360. In some embodiments, obtaining audio data (612) may comprise receiving audio data from an external device, for example through a communication device such as communication modules 340, external communication modules 540, internal communication modules 550, and so forth. In some embodiments, obtaining audio data (612) may comprise reading audio data from memory, such as memory units 320, shared memory modules 520, and so forth. In some embodiments, obtaining audio data (612) may comprise obtaining audio data captured: continuously; at selected times; when specific conditions are met; upon a detection of a trigger; and so forth.

In some embodiments, obtaining audio data (612) may further comprise analyzing the audio data to obtain preprocessed audio data. One of ordinary skill in the art will recognize that the followings are examples, and that the audio data may be preprocessed using other kinds of preprocessing methods. In some examples, the audio data may be preprocessed by transforming the audio data using a transformation function to obtain a transformed audio data, and the preprocessed audio data may comprise the transformed audio data. For example, the transformation function may comprise a multiplication of a vectored time series representation of the audio data with a transformation matrix. For example, the transformation function may comprise convolutions, audio filters (such as low-pass filters, high-pass filters, band-pass filters, all-pass filters, etc.), nonlinear functions, and so forth. In some examples, the audio data may be preprocessed by smoothing the audio data, for example using Gaussian convolution, using a median filter, and so forth. In some examples, the audio data may be preprocessed to obtain a different representation of the audio data. For example, the preprocessed audio data may comprise: a representation of at least part of the audio data in a frequency domain; a Discrete Fourier Transform of at least part of the audio data; a Discrete Wavelet Transform of at least part of the audio data; a time/frequency representation of at least part of the audio data; a spectrogram of at least part of the audio data; a log spectrogram of at least part of the audio data; a Mel-Frequency Cepstrum of at least part of the audio data; a sonogram of at least part of the audio data; a periodogram of at least part of the audio data; a representation of at least part of the audio data in a lower dimension; a lossy representation of at least part of the audio data; a lossless representation of at least part of the audio data; a time order series of any of the above; any combination of the above; and so forth. In some examples, the audio data may be preprocessed to extract audio features from the audio data. Some examples of such audio features may include: auto-correlation; number of zero crossings of the audio signal; number of zero crossings of the audio signal centroid; MP3 based features; rhythm patterns; rhythm histograms; spectral features, such as spectral centroid, spectral spread, spectral skewness, spectral kurtosis, spectral slope, spectral decrease, spectral roll-off, spectral variation, etc.; harmonic features, such as fundamental frequency, noisiness, inharmonicity, harmonic spectral deviation, harmonic spectral variation, tristimulus, etc.; statistical spectrum descriptors; wavelet features; higher level features; perceptual features, such as total loudness, specific loudness, relative specific loudness, sharpness, spread, etc.; energy features, such as total energy, harmonic part energy, noise part energy, etc.; temporal features; and so forth.

In some embodiments, analysis of the audio data may be performed on the raw audio data and/or on the preprocessed audio data. In some examples, the analysis of the audio data and/or the preprocessed audio data may be based, at least in part, on one or more rules, functions, procedures, neural networks, inference models, and so forth. The rules, functions, procedures, neural networks, and inference models may be applied to the raw audio data and/or to the preprocessed audio data. Some examples of such inference models may comprise: a classification model; a regression model; an inference model preprogrammed manually; a result of training algorithms, such as machine learning algorithms and/or deep learning algorithms, on training examples, where the training examples may include examples of data instances, and in some cases, each data instance may be labeled with a corresponding desired label and/or result; and so forth.

In some embodiments, obtaining visual data (614) may comprise obtaining and/or capturing visual data, such as: images; video frames; sequence of images; video clips; continuous videos; 3D images; 3D video frames; sequence of 3D images; 3D video clips; continuous 3D video clips; any combination of the above; and so forth. In some embodiments, visual data obtained by module 614 may be synchronized with audio data obtained by module 612. In some embodiments, obtaining visual data (614) may comprise obtaining and/or capturing visual data from one or more image sensors, for example using image sensors 371. In some embodiments, the one or more image sensors may comprise one or more wearable image sensors, such as image sensors 371 included a wearable version of apparatus 300. In some embodiments, obtaining visual data (614) may comprise receiving visual data from an external device, for example through a communication device such as communication modules 340, external communication modules 540, internal communication modules 550, and so forth. In some embodiments, obtaining visual data (614) may comprise reading visual data from memory, such as memory units 320, shared memory modules 520, and so forth. In some embodiments, obtaining visual data (614) may comprise obtaining visual data captured: continuously; at selected times; when specific conditions are met; upon a detection of a trigger; and so forth.

In some embodiments, obtaining visual data (614) may further comprise analyzing the visual data to obtain preprocessed visual data. One of ordinary skill in the art will recognize that the followings are examples, and that the visual data may be preprocessed using other kinds of preprocessing methods. In some examples, the visual data may be preprocessed by transforming the visual data using a transformation function to obtain a transformed visual data, and the preprocessed visual data may comprise the transformed visual data. For example, the transformation function may comprise convolutions, visual filters (such as low-pass filters, high-pass filters, band-pass filters, all-pass filters, etc.), nonlinear functions, and so forth. In some examples, the visual data may be preprocessed by smoothing the visual data, for example using Gaussian convolution, using a median filter, and so forth. In some examples, the visual data may be preprocessed to obtain a different representation of the visual data. For example, the preprocessed visual data may comprise: a representation of at least part of the visual data in a frequency domain; a Discrete Fourier Transform of at least part of the visual data; a Discrete Wavelet Transform of at least part of the visual data; a time/frequency representation of at least part of the visual data; a representation of at least part of the visual data in a lower dimension; a lossy representation of at least part of the visual data; a lossless representation of at least part of the visual data; a time order series of any of the above; any combination of the above; and so forth. In some examples, the visual data may be preprocessed to extract edges, and the preprocessed visual data may comprise information based on and/or related to the extracted edges. In some examples, the visual data may be preprocessed to extract visual features from the visual data. Some examples of such visual features may comprise information based on and/or related to: edges; corners; blobs; ridges; Scale Invariant Feature Transform (SIFT) features; temporal features; and so forth.

In some embodiments, analysis of the visual data may be performed on the raw visual data and/or on the preprocessed visual data. In some examples, the analysis of the visual data and/or the preprocessed visual data may be based, at least in part, on one or more rules, functions, procedures, neural networks, inference models, and so forth. The rules, functions, procedures, neural networks, and inference models may be applied to the raw visual data and/or to the preprocessed visual data. Some examples of such inference models may comprise: a classification model; a regression model; an inference model preprogrammed manually; a result of training algorithms, such as machine learning algorithms and/or deep learning algorithms, on training examples, where the training examples may include examples of data instances, and in some cases, each data instance may be labeled with a corresponding desired label and/or result; and so forth.

In some embodiments, obtaining physiological data (616) may comprise obtaining and/or capturing physiological data from one or more physiological sensors, for example using physiological sensors 372. In some examples, one or more physiological sensors may comprise one or more wearable physiological sensors, such as physiological sensors 372 included in a wearable version of apparatus 300. Some examples of such physiological sensors may include: glucose sensors, electrocardiogram sensors, electroencephalogram sensors, electromyography sensors, odor sensors, respiration sensors, blood pressure sensors, pulse oximeter sensors, heart rate sensors, perspiration sensors, and so forth. In some embodiments, physiological data obtained by module 616 may be synchronized with audio data obtained by module 612 and/or with visual data obtained by module 614. In some embodiments, obtaining physiological data (616) may comprise receiving physiological data from an external device, for example through a communication device such as communication modules 340, external communication modules 540, internal communication modules 550, and so forth. In some embodiments, obtaining physiological data (616) may comprise reading physiological data from memory, such as memory units 320, shared memory modules 520, and so forth. In some embodiments, obtaining physiological data (616) may comprise obtaining physiological data captured: continuously; at selected times; when specific conditions are met; upon a detection of a trigger; and so forth.

In some embodiments, obtaining physiological data (616) may further comprise analyzing physiological data to obtain preprocessed physiological data. One of ordinary skill in the art will recognize that the followings are examples, and that the physiological data may be preprocessed using other kinds of preprocessing methods. In some examples, the physiological data may be preprocessed by transforming the physiological data using a transformation function to obtain a transformed physiological data, and the preprocessed physiological data may comprise the transformed physiological data. For example, the transformation function may comprise convolutions, filters (such as low-pass filters, high-pass filters, band-pass filters, all-pass filters, etc.), nonlinear functions, and so forth. In some examples, the physiological data may be preprocessed by smoothing the physiological data, for example using Gaussian convolution, using a median filter, and so forth. In some examples, the physiological data may be preprocessed to obtain a different representation of the physiological data. For example, the preprocessed physiological data may comprise: a representation of at least part of the physiological data in a frequency domain; a Discrete Fourier Transform of at least part of the physiological data; a Discrete Wavelet Transform of at least part of the physiological data; a time/frequency representation of at least part of the physiological data; a representation of at least part of the physiological data in a lower dimension; a lossy representation of at least part of the physiological data; a lossless representation of at least part of the physiological data; a time order series of any of the above; any combination of the above; and so forth. In some examples, the physiological data may be preprocessed to detect features within the physiological data, and the preprocessed physiological data may comprise information based on and/or related to the detected features.

In some embodiments, analysis of the physiological data may be performed on the raw physiological data and/or on the preprocessed physiological data. In some examples, the analysis of the physiological data and/or the preprocessed physiological data may be based, at least in part, on one or more rules, functions, procedures, neural networks, inference models, and so forth. The rules, functions, procedures, neural networks, and inference models may be applied to the raw physiological data and/or to the preprocessed physiological data. Some examples of such inference models may comprise: a classification model; a regression model; an inference model preprogrammed manually; a result of training algorithms, such as machine learning algorithms and/or deep learning algorithms, on training examples, where the training examples may include examples of data instances, and in some cases, each data instance may be labeled with a corresponding desired label and/or result; and so forth.

In some embodiments, obtaining positioning data (618) may comprise obtaining and/or capturing positioning data from one or more sensors, for example using positioning sensors 374. In some examples, the one or more sensors may comprise one or more wearable sensors, such as positioning sensors 374 included in a wearable version of apparatus 300. In some embodiments, positioning data obtained by module 618 may be synchronized with audio data obtained by module 612 and/or with visual data obtained by module 614 and/or with physiological data obtained by module 616. In some embodiments, obtaining positioning data (618) may comprise receiving positioning data from an external device, for example through a communication device such as communication modules 340, external communication modules 540, internal communication modules 550, and so forth. In some embodiments, obtaining positioning data (618) may comprise reading positioning data from memory, such as memory units 320, shared memory modules 520, and so forth. In some embodiments, obtaining positioning data (618) may comprise obtaining positioning data captured: continuously; at selected times; when specific conditions are met; upon a detection of a trigger; and so forth.

In some embodiments, obtaining positioning data (618) may further comprise analyzing positioning data to obtain preprocessed positioning data. One of ordinary skill in the art will recognize that the followings are examples, and that the positioning data may be preprocessed using other kinds of preprocessing methods. In some examples, the positioning data may be preprocessed by transforming the positioning data using a transformation function to obtain a transformed positioning data, and the preprocessed positioning data may comprise the transformed positioning data. For example, the transformation function may comprise convolutions, filters (such as low-pass filters, high-pass filters, band-pass filters, all-pass filters, etc.), nonlinear functions, and so forth. In some examples, the positioning data may be preprocessed by smoothing the positioning data, for example using Gaussian convolution, using a median filter, and so forth. In some examples, the positioning data may be preprocessed to obtain a different representation of the positioning data. For example, the preprocessed positioning data may comprise: a representation of at least part of the positioning data in a frequency domain; a Discrete Fourier Transform of at least part of the positioning data; a Discrete Wavelet Transform of at least part of the positioning data; a time/frequency representation of at least part of the positioning data; a representation of at least part of the positioning data in a lower dimension; a lossy representation of at least part of the positioning data; a lossless representation of at least part of the positioning data; a time order series of any of the above; any combination of the above; and so forth. In some examples, the positioning data may be preprocessed to detect features and/or patterns within the positioning data, and the preprocessed positioning data may comprise information based on and/or related to the detected features and/or the detected patterns. In some examples, the positioning data may be preprocessed by comparing the positioning data to positions of known sites to determine sites from the positioning data.

In some embodiments, analysis of the positioning data may be performed on the raw positioning data and/or on the preprocessed positioning data. In some examples, the analysis of the positioning data and/or the preprocessed positioning data may be based, at least in part, on one or more rules, functions, procedures, neural networks, inference models, and so forth. The rules, functions, procedures, neural networks, and inference models may be applied to the raw positioning data and/or to the preprocessed positioning data. Some examples of such inference models may comprise: a classification model; a regression model; an inference model preprogrammed manually; a result of training algorithms, such as machine learning algorithms and/or deep learning algorithms, on training examples, where the training examples may include examples of data instances, and in some cases, each data instance may be labeled with a corresponding desired label and/or result; and so forth.

In some embodiments, obtaining motion data (620) may comprise obtaining and/or capturing motion data from one or more sensors, for example using accelerometers 373 and/or gyroscopes and/or positioning sensors 374. In some examples, the one or more sensors may comprise one or more wearable sensors, such as accelerometers 373 and/or gyroscopes and/or positioning sensors 374 included in a wearable version of apparatus 300. In some embodiments, motion data obtained by module 620 may be synchronized with audio data obtained by module 612 and/or with visual data obtained by module 614 and/or with physiological data obtained by module 616 and/or with positioning data obtained by module 618. In some embodiments, obtaining motion data (620) may comprise receiving motion data from an external device, for example through a communication device such as communication modules 340, external communication modules 540, internal communication modules 550, and so forth. In some embodiments, obtaining motion data (620) may comprise reading motion data from memory, such as memory units 320, shared memory modules 520, and so forth. In some embodiments, obtaining motion data (620) may comprise obtaining motion data captured: continuously; at selected times; when specific conditions are met; upon a detection of a trigger; and so forth.

In some embodiments, obtaining motion data (620) may further comprise analyzing motion data to obtain preprocessed motion data. One of ordinary skill in the art will recognize that the followings are examples, and that the motion data may be preprocessed using other kinds of preprocessing methods. In some examples, the motion data may be preprocessed by transforming the motion data using a transformation function to obtain a transformed motion data, and the preprocessed motion data may comprise the transformed motion data. For example, the transformation function may comprise convolutions, filters (such as low-pass filters, high-pass filters, band-pass filters, all-pass filters, etc.), nonlinear functions, and so forth. In some examples, the motion data may be preprocessed by smoothing the motion data, for example using Gaussian convolution, using a median filter, and so forth. In some examples, the motion data may be preprocessed to obtain a different representation of the motion data. For example, the preprocessed motion data may comprise: a representation of at least part of the motion data in a frequency domain; a Discrete Fourier Transform of at least part of the motion data; a Discrete Wavelet Transform of at least part of the motion data; a time/frequency representation of at least part of the motion data; a representation of at least part of the motion data in a lower dimension; a lossy representation of at least part of the motion data; a lossless representation of at least part of the motion data; a time order series of any of the above; any combination of the above; and so forth. In some examples, the motion data may be preprocessed to detect features and/or motion patterns within the motion data, and the preprocessed motion data may comprise information based on and/or related to the detected features and/or the detected motion patterns.

In some embodiments, analysis of the motion data may be performed on the raw motion data and/or on the preprocessed motion data. In some examples, the analysis of the motion data and/or the preprocessed motion data may be based, at least in part, on one or more rules, functions, procedures, neural networks, inference models, and so forth. The rules, functions, procedures, neural networks, and inference models may be applied to the raw motion data and/or to the preprocessed motion data. Some examples of such inference models may comprise: a classification model; a regression model; an inference model preprogrammed manually; a result of training algorithms, such as machine learning algorithms and/or deep learning algorithms, on training examples, where the training examples may include examples of data instances, and in some cases, each data instance may be labeled with a corresponding desired label and/or result; and so forth.

In some embodiments, obtaining textual information (650) may comprise analyzing the audio data and/or the preprocessed audio data to obtain information, including textual information. In some examples, obtaining textual information (650) may comprise using speech to text algorithms to transcribe spoken language in the audio data. In some examples, obtaining textual information (650) may comprise: analyzing the audio data and/or the preprocessed audio data to identify words, keywords, and/or phrases in the audio data, for example using sound recognition algorithms; and representing the identified words, keywords, and/or phrases, for example in a textual manner, using graphical symbols, in a vector representation, as a pointer to a database of words, keywords, and/or phrases, and so forth. In some examples, obtaining textual information (650) may comprise: analyzing the audio data and/or the preprocessed audio data using sound recognition algorithms to identify nonverbal sounds in the audio data; and describing the identified nonverbal sounds, for example in a textual manner, using graphical symbols, as a pointer to a database of sounds, and so forth. In some examples, obtaining textual information (650) may comprise using acoustic fingerprint based algorithms to identify items in the audio data. Some examples of such items may include: songs, melodies, tunes, sound effects, and so forth. The identified items may be represented: in a textual manner; using graphical symbols; as a pointer to a database of items; and so forth. In some examples, obtaining textual information (650) may comprise analyzing the audio data and/or the preprocessed audio data to obtain properties of voices present in the audio data, including properties associated with: pitch, intensity, tempo, rhythm, prosody, flatness, and so forth. In some examples, obtaining textual information (650) may comprise: recognizing different voices, for example in different portions of the audio data; and/or identifying different properties of voices present in different parts of the audio data. As a result, different portions of the textual information may be associated with different voices and/or different properties. In some examples, different portions of the textual information may be associated with different textual formats, such as layouts, fonts, font sizes, font styles, font formats, font typefaces, and so forth. For example, different portions of the textual information may be associated with different textual formats based on different voices and/or different properties associated with the different portions of the textual information. Some examples of such speech to text algorithms and/or sound recognition algorithms may include: hidden Markov models based algorithms; dynamic time warping based algorithms; neural networks based algorithms; machine learning and/or deep learning based algorithms; and so forth.

In some embodiments, obtaining spatial information (652) may comprise obtaining spatial information associated with the audio data. In some examples, the obtained spatial information may be synchronized with the audio data. In some examples, the obtained spatial information may comprise location information related to the location of: one or more sound sources associated with sounds present in the audio data; one or more speakers associated with speech present in the audio data; and so forth. Some examples of location information may include information associated with one or more of: direction; distance; 2D position; 3D position; absolute position; relative position; any combination of the above; and so forth. In some examples, location information may be: associated with a single point in time; associated with multiple points in time; associated with a range of times; continuous; and so forth.

In some embodiments, obtaining spatial information (652) may comprise analyzing the audio data and/or the preprocessed audio data to obtain spatial information. In some embodiments, obtaining spatial information (652) may comprise analyzing the audio data and/or the preprocessed audio data using sound localization algorithms to obtain location information associated with sounds and/or speech present in the audio data. Some examples of sound localization algorithms may include: steered beamformer approach based algorithms; collocated microphone array based algorithms; binaural hearing learning based algorithms; head related transfer function based algorithms; cross power spectrum phase based algorithms; 2D sensor line array based algorithms; hierarchical algorithms; neural networks based algorithms; triangulation algorithms; time of arrival based algorithms; particle velocity based algorithms; and so forth. In some embodiments, obtaining spatial information (652) may comprise obtaining estimated direction of arrival associated with the audio data, and in some cases, the location information may be based on the estimated direction of arrival.

In some embodiments, obtaining spatial information (652) may comprise analyzing the visual data and/or the preprocessed visual data to obtain spatial information, such as: location information associated with one or more sound sources visible in the visual data; location information associated with one or more speakers visible in the visual data; and so forth. In some examples, a speaker location in 2D image and/or 2D video may be detected using detection algorithms, for example by face detection algorithms, by algorithms that detect lips movements, etc., and location information may be calculated, for example: a direction may be calculated based on the based on the speaker location in the 2D image and/or 2D video and/or the capturing parameters; a distance may be calculated based on the based on the speaker location in the 2D image and/or 2D video and/or the capturing parameters; and so on. In some examples, a speaker location in 3D image and/or 3D video may be detected using detection algorithms, therefore obtaining location information, such as direction, distance, position, and so forth. In some examples, stereopsis methods may be applied on the visual data and/or the preprocessed visual data to obtain the location information.

In some embodiments, obtaining spatial information (652) may comprise associating a speaker visible in the visual data with one or more portions of speech in the audio data. For example, detection of lips movement at a certain time may hint an association of the speaker moving the lips with speech present in the audio data at the same time. In an additional example, correspondence between an estimated direction associated with the audio data and an estimated direction of a person and/or a face appearing in the visual data may hint an association of the person and/or face with speech present in the audio data at the same time. In some examples, these hints may be aggregated, and after a certain confidence threshold is exceeded, a speaker may be associated with specific portions of speech in the audio data. In some examples, the confidence level may be based, at least in part, on correspondence between speaker diarization of the audio data and on appearance of specific people in the visual data over time, for example based on tracking algorithms, based on face recognition algorithms, and so forth. In some examples, a database of associations of face information with voice profiles may be accessed, a speaker may be associated with one or more portions of speech in the audio data that match the speaker voice profile, the speaker may be detected in the visual data based on the face information, and an association may be made between the one or more portions of speech matching the voice profile and information based on the detection in the visual data.

In some embodiments, obtaining spatial information (652) may comprise obtaining directional information associated of one speaker with respect to another speaker. For example, the directional information may comprise information associated with at least one of: relative direction, relative distance, relative position, and so forth. In some examples, location information for two speakers may be obtained, for example as described above, and relative location information of one speaker with respect to another speaker may be calculated. For example, given direction and distance of the two speakers from the same point, the relative direction and distance may be obtain through subtraction of the two vectors. In another example, given two absolute positions, the relative position may be obtained through subtraction of one position from the other. In some cases, the location of a speaker may be calculated with respect to sensors, such as audio sensors 360 and/or image sensors 371, and in case the sensors are wearable sensors configured to be worn by one of the speakers, the relative location of a speaker may be based on the location information calculated for that speaker.

In some embodiments, obtaining spatial information (652) may comprise obtaining spatial orientation information associated with one or more speakers. For example, spatial orientation information may be associated with a wearer of a wearable sensor, of a speaker speaking in the captured audio data, of a person and/or a speaker visible in the captured visual data, and so forth.

In some embodiments, information captured using one or more wearable sensors configured to be worn by a wearer may be obtained, and the spatial orientation information associated with the wearer may comprise the orientation of at least one wearable sensor with respect to the wearer. In some examples, the orientation of the at least one wearable sensor with respect to the wearer may be obtained using: an accelerometer, such as accelerometer 373; a gyroscope; an image sensor, such as image sensor 371; and so forth. In some examples, the at least one wearable sensor may comprise a wearable image sensor, such as a wearable version of image sensor 371, and the orientation of the at least one wearable sensor with respect to the wearer may be obtained: by detecting the horizon in the captured images, by identifying in the captured images a specific body part of the wearer (such as head, torso, etc.), and so forth. In some examples, the at least one wearable sensor may comprise a wearable audio sensor, such as a wearable version of audio sensor 360, and the orientation of the at least one wearable sensor with respect to the wearer and/or the mouth of the wearer may be based on the directional information associated with the wearer, where the directional information associated with the wearer may be obtained as described above.

In some embodiments, the visual data and/or the preprocessed visual data may be analyzed to obtain spatial orientation information associated with one or more speakers. For example, the torso of a speaker may be detected, and the orientation may be obtained by determining the orientation of the torso. In another example, the head and/or face of the speaker may be detected, and the orientation may be obtained by determining the orientation of the head and/or face. In another example, at least one eye or parts of at least one eye may be detected in the visual data and/or the preprocessed visual data, and the orientation may be obtained by determining the orientation of the speaker gaze, for example using eye tracking algorithms.

In some embodiments, identifying audio portions (654) may comprise analyzing the audio data and/or the preprocessed audio data to identify one or more portions of the audio data. In some examples, an identified portion of the audio data may comprise a continuous part of the audio data or a non-continuous part of the audio data. In some examples, at least one of the one or more portions of the audio data may correspond to at least one of: a silent part of the audio data; a part of the audio data that does not contain speech; a utterance; a phoneme; a syllable; a morpheme; a word; a sentence; a conversation; a number of phonemes; a number of syllables; a number of morphemes; a number of words; a number of sentences; a number of conversations; a continuous part of the audio data corresponding to a single speaker; a non-continuous part of the audio data corresponding to a single speaker; a continuous part of the audio data corresponding to a group of speakers; a non-continuous part of the audio data corresponding to a group of speakers; and so forth.

In some embodiments, identifying audio portions (654) may comprise analyzing the audio data and/or the preprocessed audio data using one or more rules to identify one or more portions of the audio data. In some examples, at least part of the one or more rules may be read from memory. In some examples, at least part of the one or more rules may be preprogrammed manually. In some examples, at least part of the one or more rules may be the result of training algorithms, such as machine learning algorithms and/or deep learning algorithms, on training examples. The training examples may include examples of data instances, and in some cases, each data instance may be labeled with a corresponding desired label and/or result. In some embodiments, the identification of the one or more portions of the audio data may be based, at least in part, on the output of one or more neural networks.

In some embodiments, identifying audio portions (654) may comprise: analyzing the audio data and/or the preprocessed audio data to obtain textual information, for example using module 650; and analyzing of the textual information to identify one or more portions of the audio data. For example, the textual information may comprise a transcription of at least part of the audio data. The textual information may be analyzed in order to identify one or more portions of the textual information corresponding to at least one of: part of the textual information that does not contain meaningful text; a utterance; a phoneme; a syllable; a morpheme; a word; a sentence; a conversation; a number of phonemes; a number of syllables; a number of morphemes; a number of words; a number of sentences; a number of conversations; continuous part of the textual information corresponding to a single speaker; non-continuous part of the textual information corresponding to a single speaker; continuous part of the textual information corresponding to a group of speakers; non-continuous part of the textual information corresponding to a group of speakers; and so forth. One or more portions of the audio data corresponding to the one or more portions of the textual information may be identified. In some examples, the textual information may be analyzed using: natural language processing algorithms, neural networks algorithms, machine learning algorithms and/or deep learning algorithms, and so forth.

In some embodiments, identifying audio portions (654) may comprise analyzing the audio data and/or the preprocessed audio data to identify one or more portions of the audio data associated with a speaker. In some examples, speaker diarization algorithms may be applied to identify the speaking time of each speaker in the audio data, therefore identifying portions of the audio data associated with selected speakers. In some examples, speaker recognition algorithms may be applied to identify when a specified speaker is speaking in the audio data, and/or to identify portions of the audio data associated with selected speakers. In some cases, a speaker may be identified as the wearer of a wearable apparatus, such as a wearable version of apparatus 300. One or more portions of the audio data may be identified as associated with the wearer. One or more portions of the audio data may be identified as associated with a speaker other than the wearer. One or more portions of the audio data may be identified as associated a group of a plurality of speakers, for example where the group of a plurality of speakers does not include the wearer.

In some embodiments, identifying audio portions (654) may comprise analyzing the audio data and/or the preprocessed audio data to identify one or more portions of the audio data based, at least in part, on spatial information associated with the audio data. In some examples, one or more portions of the audio data associated with a selected direction and/or selected range of directions may be identified. For example, the spatial information may comprise directional information of sound sources associated with sounds present in the audio data, directional information associated with speech present in the audio data, and/or directional information associated with speakers, and the one or more portions of the audio data that contain sounds and/or speech associated with a selected direction and/or selected range of directions may be identified. For example, the audio data may comprise audio data captured using a wearable apparatus comprising one or more audio sensors, such as a wearable version of apparatus 300. In such example, the wearer of the wearable apparatus may be associated with a selected direction and/or selected range of directions, and one or more portions of the audio data that contain sounds and/or speech associated with the selected direction and/or the selected range of directions may be identified.

In some embodiments, obtaining prosodic information (656) may comprise analyzing the audio data and/or the preprocessed audio data to obtain prosodic information. The prosodic information may be associated with a group of one or more portions of the audio data and/or with one or more points in time and/or with one or more points in the audio data. For example, the prosodic information may be associated with a group of one or more portions of the audio data that were identified, for example as described above, as associated with a given speaker, a given conversation, a given context, and so forth. In some examples, a group of one or more portions of the audio data and/or a group of one or more portions of the preprocessed audio data may be analyzed to obtain prosodic information associated with a group of one or more portions of the audio data.

In some embodiments, the prosodic information may comprise information associated with speech rhythm. For example, duration of speech sounds may be measured. Some examples of such speech sounds may include: vowels, consonants, syllables, utterances, and so forth. In some cases, statistics related to the duration of speech sounds may be gathered. In some examples, the variance of vowel duration may be calculated. In some examples, the percentage of speech time dedicated to one type of speech sounds may be measured. In some examples, contrasts between durations of neighboring vowels may be measured.

In some embodiments, the prosodic information may comprise information associated with speech tempo. For example, speaking rate may be measured. For example, articulation rate may be measured. In some cases, the number of syllables per a unit of time may be measured, where the unit of time may include and/or exclude times of pauses, hesitations, and so forth. In some cases, the number of words per a unit of time may be measured, where the unit of time may include and/or exclude times of pauses, hesitations, and so forth. In some cases, statistics related to the rate of syllables may be gathered. In some cases, statistics related to the rate of words may be gathered.

In some embodiments, the prosodic information may comprise information associated with pitch of the voice. For example, pitch may be measured at specified times, randomly, continuously, and so forth. In some cases, statistics related to the pitch may be gathered. In some cases, pitch may be measured at different segments of speech, and statistics related to the pitch may be gathered for each type of segment separately. In some cases, the average speaking pitch over a time period may be calculated. In some cases, the minimal and/or maximal speaking pitch in a time period may be found.

In some embodiments, the prosodic information may comprise information associated with loudness of the voice. For example, the loudness may be measured as the intensity of the voice. For example, loudness may be measured at specified times, randomly, continuously, and so forth. In some cases, statistics related to the loudness may be gathered. In some cases, loudness may be measured at different segments of speech, and statistics related to the loudness may be gathered for each type of segment separately. In some cases, the average speaking loudness over a time period may be calculated. In some cases, the minimal and/or maximal speaking loudness in a time period may be found.

In some embodiments, the prosodic information may comprise information associated with intonation of the voice. For example, the pitch of the voice may be analyzed to identify rising and falling intonations. In another example, rising intonation, falling intonation, dipping intonation, and/or peaking intonation may be identified. For example, intonation may be identified at specified times, randomly, continuously, and so forth. In some cases, statistics related to the intonation may be gathered.

In some embodiments, the prosodic information may comprise information associated with a linguistic tone associated with a portion of the audio data. For example, the usage of pitch to distinguish and/or inflect words, to express emotional and/or paralinguistic information, to convey emphasis, contrast, and so forth, may be identified. Some examples of linguistic tone may include: abashed, abrasive, abusive, accepting, acquiescent, admiring, adoring, affectionate, aggravated, aghast, allusive, amused, angry, anxious, apologetic, appreciative, apprehensive, approving, arch, ardent, argumentative, artificial, ashamed, audacious, authoritative, awe-struck, bantering, begrudging, bemused, benevolent, biting, bitter, blithe, boastful, bored, bristling, brusque, calm, candid, caring, caustic, cavalier, cheerful, childish, child-like, clipped, cold, compassionate, complimentary, condemning, condescending, confident, contemptuous, conversational, coy, critical, curt, cutting, cynical, denunciatory, despairing, detached, didactic, disappointed, disbelieving, disconcerted, discouraged, disdainful, disgusted, disinterested, disparaging, disrespectful, distracted, doubtful, dramatic, dreamy, dry, ecstatic, embarrassed, energetic, entranced, enthusiastic, eulogistic, excited, exhilarated, exultant, facetious, fanciful, fearful, flippant, fond, forceful, friendly, frightened, ghoulish, giddy, gleeful, glum, grim, guarded, guilty, happy, harsh, hateful, haughty, heavy-hearted, hollow, horrified, humorous, hypercritical, indifferent, indignant, indulgent, inflammatory, insulting, ironic, irreverent, irritated, joking, joyful, languorous, languid, laudatory, light-hearted, lingering, loving, manipulative, marveling, melancholy, mistrustful, mocking, mysterious, naive, negative, neutral, nostalgic, objective, passionate, patronizing, peaceful, pessimistic, pitiful, playful, poignant, positive, pragmatic, proud, provocative, questioning, rallying, reflective, reminiscing, reproachful, resigned, respectful, restrained, reticent, reverent, ridiculing, romantic, rueful, sad, sarcastic, sardonic, satiric, satisfied, seductive, self-critical, self-dramatizing, self-justifying, self-mocking, self-pitying, self-satisfied, sentimental, serious, severe, sharp, shocked, silly, sly, smug, solemn, somber, stentorian, stern, straightforward, strident, stunned, subdued, surprised, swaggering, sweet, sympathetic, taunting, teasing, tense, thoughtful, threatening, tired, touchy, trenchant, uncertain, understated, upset, urgent, vexed, vibrant, wary, whimsical, withering, wry, zealous, and so forth.

In some embodiments, the prosodic information may comprise information associated with stress of the voice. For example, loudness of the voice and/or vowels length may be analyzed to identify an emphasis given to a specific syllable. In another example, loudness of the voice and pitch may be analyzed to identify emphasis on specific words, phrases, sentences, and so forth. In an additional example, loudness, vowel length, articulation of vowels, pitch, and so forth may be analyzed to identify emphasis associated with a specific time of speaking, with specific portions of speech, and so forth.

In some embodiments, the prosodic information may comprise information associated with pauses. For example, length of pauses may be measured. In some cases, statistics related to the length of pauses may be gathered.

In some embodiments, the prosodic information may comprise information associated with timbre of the voice.

For example, voice brightness may be identified. As another example, formant structure associated with the pronunciation of the different sounds may be identified. In some embodiments, the prosodic information may comprise information associated with accent. For example, the type of accent may be identified. In some embodiments, the prosodic information may comprise an identification of flatness level of a voice.

In some embodiments, obtaining prosodic information (656) may comprise analyzing the audio data and/or the preprocessed audio data using one or more rules to obtain prosodic information. In some examples, at least part of the one or more rules may be read from memory. In some examples, at least part of the one or more rules may be received from an external device, for example using a communication device. In some examples, at least part of the one or more rules may be preprogrammed manually. In some examples, at least part of the one or more rules may be the result of training algorithms, such as machine learning algorithms and/or deep learning algorithms, on training examples. The training examples may include examples of data instances, and in some cases, each data instance may be labeled with a corresponding desired label and/or result. For example, the training examples may include audio samples that contain speech, and be labeled according to the prosodic properties of the contained speech. In some embodiments, the identification of the prosodic information may be based, at least in part, on the output of one or more neural networks.

In some embodiments, identifying conversations (658) may comprise obtaining an indication that two or more speakers are engaged in conversation. For example, speaker diarization information may be obtained, for example by using a speaker diarization algorithm. The speaker diarization information may be analyzed in order to identify which speakers are engaged in conversation at what time, for example by detecting a sequence in time in which two or more speakers talk in turns. In another example, clustering algorithms may be used to analyze the speaker diarization information and divide the speaker diarization information to conversations. In another example, the speaker diarization information may be divided when no activity is recorder in the speaker diarization information for duration longer than a selected threshold.

In some embodiments, identifying conversations (658) may comprise analyzing the audio data and/or the preprocessed audio data to identify a conversation in the audio data. Some examples of such analysis methods may include: the application of speaker diarization algorithms in order to obtain speaker diarization information, and analyzing the speaker diarization information as described above; the usage of neural networks trained to detect conversations within audio data, where the input to the neural networks may comprise the audio data and/or the preprocessed audio data; analyzing the audio data and/or the preprocessed audio data to obtain textual information, for example using module 650, and analyzing of the textual information to identify conversations, for example using textual conversation identification algorithms; and so forth. In some examples, speakers taking part in that conversation may be identified, for example using speaker recognition algorithms. Some examples of such speaker recognition algorithms may include: pattern recognition algorithms; hidden Markov models based algorithms; mixture of Gaussians based algorithms; pattern matching based algorithms; neural networks based algorithms; quantization based algorithms; machine learning and/or deep learning based algorithms; and so forth.

In some embodiments, identifying conversations (658) may comprise analyzing the visual data and/or the preprocessed visual data to identify a conversation involving two or more speakers visible in the visual data, and possibly in order to identify the speakers taking part in the conversation, for example using face recognition algorithms. Some examples of such analysis may comprise: usage of action recognition algorithms; usage of lips reading algorithms; and so forth.

In some embodiments, identifying conversations (658) may comprise analyzing information coming from variety of sensors, for example identifying conversations based on an analysis of audio data and visual data.

In some embodiments, identifying speakers (660) may comprise obtaining identifying information associated with one or more speakers. In some examples, identifying speakers (660) may identify the name of one or more speakers, for example by accessing a database that comprises names and identifying audible and/or visual features. In some examples, identifying speakers (660) may identify demographic information associated with one or more speakers, such as age, sex, and so forth. In some embodiments, identifying speakers (660) may comprise analyzing the input data using one or more rules to determine demographic information associated with one or more speakers, such as age, sex, and so forth. In some examples, at least part of the one or more rules may be read from memory. In some examples, at least part of the one or more rules may be preprogrammed manually. In some examples, at least part of the one or more rules may be the result of training algorithms, such as machine learning algorithms and/or deep learning algorithms, on training examples. The training examples may include examples of data instances, and in some cases, each data instance may be labeled with a corresponding desired label and/or result. For example, the training examples may include audio samples that contain speech, and be labeled according to the age and/or sex of the speaker. In another example, the training examples may include images that contain faces, and be labeled according to the age and/or sex of the faces. In some embodiments, the determining demographic information may be based, at least in part, on the output of one or more neural networks.

In some embodiments, identifying speakers (660) may comprise analyzing the audio data and/or the preprocessed audio data to identify one or more speakers and/or to identify information associated with one or more speakers, for example using speaker recognition algorithms. Some examples of such speaker recognition algorithms may include: pattern recognition algorithms; hidden Markov models based algorithms; mixture of Gaussians based algorithms; pattern matching based algorithms; neural networks based algorithms; quantization based algorithms; machine learning and/or deep learning based algorithms; and so forth.

In some embodiments, identifying speakers (660) may comprise analyzing the visual data and/or the preprocessed visual data to detect one or more speakers and/or to identify one or more speakers and/or to identify information associated with one or more speakers, for example using lips movement detection algorithms, face recognition algorithms, and so forth.

In some embodiments, measuring lengths (664) may comprise obtaining a measurement associated with the length of one or more segments of the audio data, or a measurement associated with the length of information associated with one or more segments of the audio data, for example by analyzing the audio data and/or the preprocessed audio data.

In some embodiments, measuring lengths (664) may comprise obtaining a measurement associated with the length of time of at least one of the following segments of the audio data: the entire audio data; a silent part of the audio data; a part of the audio data that does not contain speech; a part of the audio data that contains speech; a utterance; a phoneme; a syllable; a morpheme; a word; a sentence; a question; a conversation; a number of phonemes; a number of syllables; a number of morphemes; a number of words; a number of sentences; a number of conversations; a continuous part of the audio data; a non-continuous part of the audio data; a continuous part of the audio data corresponding to a single speaker; a non-continuous part of the audio data corresponding to a single speaker; a continuous part of the audio data corresponding to a group of speakers; a non-continuous part of the audio data corresponding to a group of speakers; any combination of the above; and so forth.

In some embodiments, measuring lengths (664) may comprise obtaining a measurement associated with the length of a segment of the audio data, or a measurement associated with the length of information associated with a segment of the audio data, may be measured by counting the number of objects contained within the segment, or within the information associated with the segment. Some examples of such objects may include: a phoneme; a syllable; a morpheme; a word; a utterance; a sentence; a question; a conversation; and so forth. For example, a length of syllable may be measured by counting the number of phonemes contained within the syllable. In another example, a length of a morpheme may be measured by counting the number of phonemes or syllables contained within the morpheme. In an additional example, the length of a word may be measured by counting the number of phonemes, syllables, or morphemes contained within the word. In another example, the length of a utterance, a sentence or a question may be measured by counting the number of phonemes, syllables, morphemes or words contained within the utterance, the sentence, or the question. In an additional example, the length of a conversation or a part of a conversation may be measured by counting the number of phonemes, syllables, morphemes, words, utterances, sentences, or questions contained within the conversation or the part of a conversation. In another example, the length of a part of the audio data corresponding to a single speaker may be measured by counting the number of phonemes, syllables, morphemes, words, utterances, sentences, questions or conversations contained within the part of the audio data corresponding to a single speaker.

In some embodiments, measuring lengths (664) may comprise analyzing the audio data and/or the preprocessed audio data and/or information associated with a segment of the audio data using one or more rules. In some examples, at least part of the one or more rules may be read from memory. In some examples, at least part of the one or more rules may be preprogrammed manually. In some examples, at least part of the one or more rules may be the result of training algorithms, such as machine learning algorithms and/or deep learning algorithms, on training examples. The training examples may include examples of data instances, and in some cases, each data instance may be labeled with a corresponding desired label and/or result. In some embodiments, measuring lengths (664) may comprise the usage of one or more neural networks, and the obtained measurements may be based, at least in part, on the output of the one or more neural networks. In some embodiments, measuring lengths (664) may comprise analyzing the audio data and/or the preprocessed audio data and/or information associated with a segment of the audio data using one or more regression models.

In some embodiments, measuring lengths (664) may comprise analyzing the audio data and/or the preprocessed audio data to obtain textual information, for example using module 650; and analyzing of the textual information to obtain a measurement associated with the length of one or more segments of the audio data, or a measurement associated with the length of information associated with one or more segments of the audio data. For example, the textual information may comprise a transcription of at least part of the audio data. The transcription may be analyzed in order to identify one or more objects, such as: letters; syllables; morphemes; words; utterances; sentences; questions; conversations; and so forth. The measurement may be based, at least in part, on the number of objects identified within a segment of the transcription, on the number of objects associated with a segment of the audio data, and so forth.

In some examples, the measurement associated with the length of one or more segments of the audio data, and/or the measurement associated with the length of information associated with one or more segments of the audio data, may comprise information related to at least one of: the mean length; the variance of the length; the distribution of lengths; statistics related to the length; histogram of lengths; and so forth.

In some embodiments, identifying context (680) may comprise obtaining context information. For example, identifying context (680) may comprise analyzing input data using one or more rules to identify context information and/or parameters of the context information. For example, the input data may include one or more of: audio data; preprocessed audio data; textual information; visual data; preprocessed visual data; physiological data; preprocessed physiological data; positioning data; preprocessed positioning data; motion data; preprocessed motion data; user input; and so forth. In some examples, at least part of the one or more rules may be read from memory. In some examples, at least part of the one or more rules may be preprogrammed manually. In some examples, at least part of the one or more rules may be the result of training algorithms, such as machine learning algorithms and/or deep learning algorithms, on training examples. The training examples may include examples of input data instances, and in some cases, each input data instance may be labeled with a corresponding desired label and/or result, such as desired context information and/or desired parameters of the context information. In some embodiments, the identification of the context information and/or parameters of the context information may be based, at least in part, on the output of one or more neural networks. In some embodiments, prototypes may be used, the most similar prototype to the input data may be selected, and the context information and/or parameters of the context information may be based, at least in part, on the selected prototype. For example, prototypes may be generated manually. In another example, prototypes may be generated by clustering input data examples, and the centroids of the clusters may be used as prototypes.

In some embodiments, identifying context (680) may comprise analyzing the audio data and/or the preprocessed audio data to identify at least part of the context information. In some examples, identifying context (680) may comprise: analyzing the audio data and/or the preprocessed audio data to obtain textual information, for example using module 650; and analyzing of the textual information to identify context information and/or parameters of the context information. For example, the textual information may comprise a transcription of at least part of the audio data, and natural language processing algorithms may be used to determine context information and/or parameters of the context information. In another example, the textual information may comprise keywords, and the context information and/or parameters of the context information may be determined based on the keywords. In some examples, identifying context (680) may comprise determining the context information and/or parameters of the context information based on prosodic information, such as the prosodic information obtained using module 656.

In some embodiments, identifying context (680) may comprise analyzing the visual data and/or the preprocessed visual data to identify at least part of the context information. For example, the visual data and/or the preprocessed visual data may be analyzed to identify scene information, for example using visual scene recognition algorithms, and the context information and/or parameters of the context information may be based, at least in part, on the scene information. For example, the visual data and/or the preprocessed visual data may be analyzed to identify one or more persons in the environment and/or demographic information related to the one or more persons, for example using face detection and/or face recognition algorithms and/or module 660, and the context information and/or parameters of the context information may be based, at least in part, on the identity of the one or more persons and/or the demographic information related to the one or more persons. For example, the visual data and/or the preprocessed visual data may be analyzed to detect one or more objects in the environment and/or information related to the one or more objects, for example using object detection algorithms, and the context information and/or parameters of the context information may be based, at least in part, on the detected one or more objects and/or the information related to the one or more objects. For example, the visual data and/or the preprocessed visual data may be analyzed to detect one or more activities in the environment and/or information related to the one or more activities, for example using activity detection algorithms, and the context information and/or parameters of the context information may be based, at least in part, on the detected one or more activities and/or the information related to the one or more activities. For example, the visual data and/or the preprocessed visual data may be analyzed to identify text in the environment, for example using optical character recognition algorithms, and the context information and/or parameters of the context information may be based, at least in part, on the identified text.

In some embodiments, identifying context (680) may comprise determining the context information and/or parameters of the context information based, at least in part, on spatial information, such as the spatial information obtained using module 652. In some embodiments, identifying context (680) may comprise determining the context information and/or parameters of the context information based, at least in part, on conversations or information related to conversations, such as the conversations identified using module 658. In some examples, context information and/or parameters of the context information may be based, at least in part, on properties of the identified conversations, such as the length of the conversation, the number of participants in the conversation, the identity of one or more participants, the topics of the conversation, keywords from the conversation, and so forth. In some embodiments, identifying context (680) may comprise determining the context information and/or parameters of the context information based, at least in part, on identifying information associated with one or more speakers, such as identifying information associated with one or more speakers obtained using module 660.

In some embodiments, providing feedbacks (690) may comprise providing one or more feedbacks to one or more users. In some examples, feedback may be provided upon a detection of: an event; an event that matches certain criterions; an event associated with properties that match certain criterions; an assessment result that match certain criterions; an item or object that matches certain criterions; an item or object associated with properties that matches certain criterions; and so forth. In some examples, the nature and/or content of the feedback may depend on: the detected event; the identified properties of the detected event; the detected item; the identified properties of the detected item; the detected object; the identified properties of the detected object; and so forth. In some examples, such events, items and/or objects may be detected by a processing unit, such as processing units 330.

In some embodiments, after providing a first feedback, one or more additional events may be identified. In such cases, providing feedbacks (690) may comprise providing additional feedbacks upon the detection of the additional events. For example, the additional feedbacks may be provided in a similar fashion to the first feedback. In some examples, the system may avoid providing additional similar feedbacks for selected time duration. In some examples, the additional feedback may be identical to the previous feedback. In some examples, the additional feedback may differ from the previous feedback, for example by being of increased intensity, by mentioning the previous feedback, and so forth.

In some embodiments, providing feedbacks (690) may comprise providing one or more feedbacks to one or more users. In some examples, feedbacks may be provided upon the identification of a trigger. In some examples, the nature of the feedback may depend on information associated with the trigger, such as the type of the trigger, properties of the identified trigger, and so forth. Examples of such triggers may include: voice commands, such as voice commands captured using audio sensors 360; press of a button; hand gestures, such as hand gestures captured using image sensors 371; and so forth. In some examples, such triggers may be identified by a processing unit, such as processing units 330.

In some embodiments, providing feedbacks (690) may comprise providing one or more feedbacks as a: visual output, for example using visual outputting units 352; audio output, for example using audio output units 351; tactile output, for example using tactile outputting units 353; electric current output; any combination of the above; and so forth. In some examples, the amount of feedbacks, the events triggering feedbacks, the content of the feedbacks, the nature of the feedbacks, etc., may be controlled by configuration. The feedbacks may be provided: by the apparatus detecting the events; through another apparatus; and so forth. In some examples, the feedbacks may be provided by a wearable apparatus, such as a wearable version of wearable apparatus 300. The feedbacks provided by the wearable apparatus may be provided to: the wearer of the wearable apparatus; one or more caregivers of the wearer of the wearable apparatus; any combination of the above; and so forth.

In some embodiments, providing reports (692) may comprise generating and/or providing one or more reports to one or more users. For example, information may be aggregated, including information related to: detected events; assessment results; identified objects; identified items; and so forth. The information may be aggregated by a processing unit, such as processing units 330. The aggregated information may be stored in memory, such as memory units 320, shared memory modules 520, and so forth. Some examples of such aggregated information may include: a log of detected events, objects, and/or items, possibly together identified properties of the detected events, objects and/or items; statistics related to the detected events, objects, and/or items; statistics related to the identified properties of the detected events, objects, and/or items; and so forth. In some embodiments, providing reports (692) may comprise generating and/or providing one or more reports based on the aggregated information. In some examples, the report may comprise: all or part of the aggregated information; a summary of the aggregated information; information derived from the aggregated information; statistics based on the aggregated information; and so forth. In some examples, the reports may include a comparison of the aggregated information to: past information, such as past performance information; goals; normal range values; and so forth.

In some embodiments, providing reports (692) may comprise providing one or more reports: in a printed form, for example using one or more printers; audibly read, for example using audio outputting units 351; visually displayed, for example using visual outputting units 352; and so forth. In some examples, the reports may be provided by or in conjunction with a wearable apparatus, such as a wearable version of apparatus 300. The generated reports may be provided to: the wearer of the wearable apparatus; one or more caregivers of the wearer of the wearable apparatus; any combination of the above; and so forth.

Figure 7:
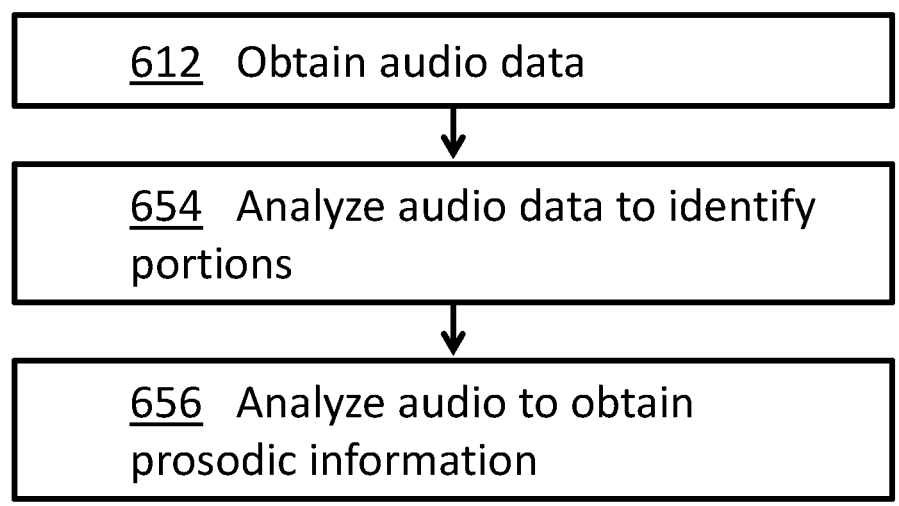
FIG. 7 illustrates an example of a process for analyzing audio to obtain prosodic information.

FIG. 7 illustrates an example of process 700 for analyzing audio to obtain prosodic information. In some examples, process 700, as well as all individual steps therein, may be performed by various aspects of: apparatus 300; server 400; cloud platform 500; computational node 510; and so forth. For example, process 700 may be performed by processing units 330, executing software instructions stored within memory units 320 and/or within shared memory modules 520. In this example, process 700 may comprise: obtaining audio data (using module 612); analyzing audio data to identify portions (using module 654); and analyzing audio data to obtain prosodic information (using module 656). In some implementations, process 700 may comprise one or more additional steps, while some of the steps listed above may be modified or excluded. For example, module 654 may be excluded from process 700. For example, process 700 may also comprise providing feedbacks (using module 690) and/or providing reports (using module 692). In some implementations, one or more steps illustrated in FIG. 7 may be executed in a different order and/or one or more groups of steps may be executed simultaneously and vice versa. For example, module 654 and/or module 656 may be executed after and/or simultaneously with module 612. For example, module 654 may be executed before, after and/or simultaneously with module 656. Examples of possible execution manners of process 700 may include: continuous execution, returning to the beginning of the process and/or to any step within the process once the process normal execution ends; periodically execution, executing the process at selected times; execution upon the detection of a trigger, where examples of such trigger may include a trigger from a user, a trigger from another process, etc.; any combination of the above; and so forth.

In some embodiments, feedback may be provided to a user, such as a wearer of the wearable apparatus, based on the prosodic information, for example using module 690. In some cases, the feedback may be provided upon the detection of a segment of the audio data associated with prosodic information that meet a certain criteria. For example, feedback may be provided: when the prosodic information associated with an audio segment produced by the wearer meet a certain criteria; when the prosodic information associated with an audio segment produced by a speaker involved in conversation with the wearer meet a certain criteria; when the duration of the audio segment that is associated with the prosodic information exceeds certain threshold; any combination of the above; and so forth. In some cases, the nature of the feedback may depend on the prosodic information, on the audio segment that is associated with the prosodic information, on a person associated with the prosodic information, and so forth. For example, the nature of the feedback may vary in intensity, in the content of visual text and/or audible speech contained in the feedback, and so forth.

In some embodiments, information related to the identified prosodic information and/or to segments of the audio data associated with the prosodic information may be aggregated, for example the aggregated information may be stored in memory. For example, a record of the prosodic information and/or segment of the audio data associated with the prosodic information may be stored in memory, for example in a log file, in a database, in a data-structure, in a container data-structure, and so forth. As more prosodic information is identified, the prosodic information may be aggregated. In some examples, the aggregated information may comprise one or more of: the prosodic information; information related to a speaker associated with the prosodic information; information related to the segment of the audio data associated with the prosodic information; audio recordings of at least part of the segment of the audio data associated with the prosodic information; statistics related to the prosodic information and/or segments of the audio data associated with the prosodic information; and so forth. In some examples, reports based on the aggregated information may be generated and/or provided to one or more users, for example using module 692. For example, a report may comprise statistics related to the prosodic information and/or segments of the audio data associated with the prosodic information. For example, a report may comprise times at which prosodic information that meets a certain condition was identified, the total duration corresponding to prosodic information that meets a certain condition, and so forth. In some examples, the reports may include a comparison of the aggregated information to: past performances, goals, normal range values, and so forth.

In some embodiments, the audio data and/or the preprocessed audio data may be analyzed in order to obtain prosodic information records associated with different speakers. For example, each prosodic information record may be associated with a specific speaker; each prosodic information record may be associated with a group of speakers; a group of prosodic information records may be associated with a specific speaker; a group of prosodic information records may be associated with a group of speakers; and so forth. Each prosodic information record may be associated with a group of one or more portions of the audio data. For example, a group of portions of the audio data may be identified as associated with a speaker or with a group of speakers. For example, two speaker engaged in conversation may be identified, and two prosodic information records associated with the two speakers may be obtained. For example, a conversation between the wearer of the wearable apparatus and a second person may be identified, a group of prosodic information records associated with the wearer may be obtained, and a group of prosodic information records associated with the second person may be obtained, and so forth.

In some embodiments, one prosodic information record may be assessed according to other prosodic information records. For example, assessing prosodic information records may comprise comparing measurements associated with speech rhythm, speech tempo, pitch, loudness, intonation, linguistic tone, stress, pauses, timbre, and so forth. In some examples, information regarding such assessments may be aggregated. Some examples of such aggregated information may include: a log of assessments; statistics regarding the assessments; and so forth. In some examples, reports based on the aggregated information may be generated. In some examples, the reports may include a comparison of the aggregated information to: past performances, goals, normal range values, and so forth. In some examples, feedbacks based on the assessment may be provided, for example to the wearer of the wearable apparatus. In some cases, the feedback may be provided when the assessment result meet certain criterions. In some cases, the nature and/or content of the feedback may depend on the assessment result.

In some embodiments, the emotional state of a speaker may be estimated based, at least in part, on the prosodic information. For example, the linguistic tone may indicate the state of mind of a speaker, the speaker attitude toward a discussed subject, and so forth. In some examples, feedbacks based on the estimated emotional state may be provided, for example to the wearer of the wearable apparatus. In some cases, the feedback may be provided when the estimated emotional state is a select emotional state, when the estimated emotional states of two speakers meet certain criterions, and so forth. In some cases, the nature and/or content of the feedback may depend on the estimated emotional state. In some examples, estimated emotional state may be aggregated over time, and reports may be provided to a user based on the aggregated information.

In some embodiments, a speaker may be associated with a presentation region, and each portion of the information may be visually presented in the presentation region associated with the speaker associated with that portion. The association of a presentation region with a speaker may be determined based, at least in part, on information associated with spatial orientation and/or position and/or direction associated with the speaker, for example in a way that will overlay information associated with a speaker over or in proximity to the speaker in an augmented reality display system. The spatial orientation and/or position of the speaker may be determined using module 652. For example, graphical symbol indicative of the linguistic tone and/or estimated emotional state of the speaker (such as a smileys, emojis, ideograms, etc.) may be presented according to the presentation region. For example, a color background and/or color scheme and/or color indicator may be presented according to the presentation region to convey the linguistic tone and/or estimated emotional state of the speaker, for example a red color may be used to convey a negative linguistic tone, a blue color may be used to convey a positive linguistic tone, and so forth.

In some embodiments, the prosodic information associated with a speaker may be analyzed to assess how socially appropriate is the prosody of a speaker. For example, a context associated with the prosodic information may be determined, for example using module 680, and the prosodic information may be assessed according to the context. In some examples, the prosodic information may be analyzed using one or more rules to obtain prosodic information, for example to assess how socially appropriate is the prosody of a speaker. In some examples, at least part of the one or more rules may be read from memory. In some examples, at least part of the one or more rules may be received from an external device, for example using a communication device. In some examples, at least part of the one or more rules may be preprogrammed manually. In some examples, at least part of the one or more rules may be the result of training algorithms, such as machine learning algorithms and/or deep learning algorithms, on training examples. The training examples may include examples of data instances, and in some cases, each data instance may be labeled with a corresponding desired label and/or result. For example, the training examples may include prosodic information records and/or context information, and be labeled according to whether it is socially appropriate. In some examples, the identification of the prosodic information may be based, at least in part, on the output of one or more neural networks. In some examples, a regression model may be used to determine the degree of inappropriateness.

In some examples, feedbacks based on whether the prosodic is socially appropriate may be provided, for example to a wearer of the wearable apparatus. In some cases, the feedback may be provided when the prosodic is appropriate and/or is inappropriate, when the appropriate and/or inappropriate prosody is prosody of a specific speaker (such as the wearer, a person engaged in conversation with the wearer, a selected person, etc.), and so forth. In some cases, the nature and/or content of the feedback may depend on the degree of inappropriateness, on the identity of the speaker associated with the appropriate and/or inappropriate prosody, and so forth. In some examples, information regarding the socially appropriateness may be aggregated over time, and reports may be provided to a user based on the aggregated information.

In some embodiments, a conversation between two people may be identified, for example using module 658. For example, a conversation between the wearer of the wearable apparatus and a second person may be identified. Prosodic information associated with one or more of the people engaged in the conversation may be obtained, for example using process 700 and/or module 656. The distance between the two people may be estimated, for example using module 652. In some examples, feedbacks may be provided, for example to a wearer of the wearable apparatus, based on the obtained prosodic information and/or the estimated distance between the two people. For example, the loudness of the voice of the wearer may be assessed according to the estimated distance, and if the voice is inappropriate to the estimated distance, feedback may be provided to the wearer. After a first feedback is provided, additional feedback may be provided, for example after a certain time duration passed and the inappropriate loudness continuous.

It will also be understood that the system according to the invention may be a suitably programmed computer, the computer including at least a processing unit and a memory unit. For example, the computer program can be loaded onto the memory unit and can be executed by the processing unit. Likewise, the invention contemplates a computer program being readable by a computer for executing the method of the invention. The invention further contemplates a machine-readable memory tangibly embodying a program of instructions executable by the machine for executing the method of the invention.

What is claimed is:

1. A system for processing audio for identifying loudness levels of speakers, the system comprising:
one or more audio sensors included in a wearable apparatus and configured to capture audio data from an environment of a wearer of the wearable apparatus; and
at least one processing unit configured to:
analyze the audio data to determine that the wearer and a second speaker are engaged in conversation;
analyze the audio data to obtain prosodic information associated with the wearer and at least part of the conversation, the prosodic information comprises an indication of a loudness level;
estimate a distance between the wearer and the second speaker;
use the estimated distance between the wearer and the second speaker and the indication of the loudness level to determine that the loudness level is inappropriate for the estimated distance;
in response to the determination that the loudness level is inappropriate for the estimated distance and the determination that the wearer and the second speaker are engaged in conversation, provide a feedback to the wearer;
obtain additional audio data captured by the one or more audio sensors after obtaining the prosodic information, the additional audio data comprising an additional part of the conversation;
estimate a second distance between the wearer and the second speaker;
analyze the additional audio data to obtain additional prosodic information associated with the wearer, the additional prosodic information comprises an additional indication of an additional loudness level;
use the estimated second distance between the wearer and the second speaker and the additional indication of the additional loudness level to determine that the additional loudness level is inappropriate for the estimated second distance;
determine an elapsed time since the feedback was provided to the wearer;
when the elapsed time is longer than a selected time duration, in response to the determination that the additional loudness level is inappropriate for the estimated second distance, provide an additional feedback to the wearer; and
when the elapsed time is shorter than the selected time duration forgo the additional feedback to the wearer.

2. The system of claim 1, wherein the prosodic information comprises information associated with at least one of speech rhythm, speech tempo and length of pauses.

3. The system of claim 1, wherein the prosodic information comprises information associated with at least one of pitch of voice and stress of voice.

4. The system of claim 1, wherein the prosodic information comprises information associated with loudness of voice.

5. The system of claim 1, wherein the prosodic information comprises information associated with at least one of intonation and tone.

6. The system of claim 1, wherein the at least one processing unit is further configured to:
analyze the audio data to determine a number of participants in the conversation; and
use the determined number of participants in the conversation in the determination that the loudness level is inappropriate for the estimated distance.

7. The system of claim 1, wherein the at least one processing unit is further configured to:
obtain contextual information based on positioning data associated with the wearable apparatus; and
use the contextual information in the determination that the loudness level is inappropriate for the estimated distance.

8. The system of claim 1, wherein the at least one processing unit is further configured to:
select a presentation region associated with the second speaker; and
based on the prosodic information and the presentation region, present a visual indication to the wearer using an augmented reality display device.

9. The system of claim 8, wherein the at least one processing unit is further configured to:
analyze the audio data to identify a linguistic tone associated with the wearer;
use the identified linguistic tone to select a color scheme; and
use the selected color scheme in the presentation of the visual indicator.

10. The system of claim 1, wherein the at least one processing unit is further configured to:
analyze the audio data to obtain a second prosodic information associated with the-second speaker and at least part of the conversation, the second prosodic information comprises a second indication of a second loudness level;
compare the indication of the loudness level and the second indication of the second loudness level; and
further base providing the information to the wearer on a result of the comparison of the loudness level and the second indication of the second loudness level.

11. The system of claim 1, wherein the at least one processing unit is further configured to:
analyze the audio data to identify the second speaker, therefore obtaining identifying information associated with the second speaker; and
further base providing the information to the wearer on the identifying information.

12. The system of claim 1, wherein the at least one processing unit is further configured to:
use the prosodic information to estimate an emotional state of the wearer; and
further base providing the information to the wearer on the estimated emotional state of the wearer.

13. A method for processing audio for identifying loudness levels of speakers, the method comprising:
capturing audio data using one or more audio sensors included in a wearable apparatus from an environment of a wearer of the wearable apparatus;
analyzing the audio data to determine that the wearer and a second speaker are engaged in conversation;
analyzing the audio data to obtain prosodic information associated with the wearer and at least part of the conversation, the prosodic information comprises an indication of a loudness level;
estimating a distance between the wearer and the second speaker;
using the estimated distance between the wearer and the second speaker and the indication of the loudness level to determine that the loudness level is inappropriate for the estimated distance;

in response to the determination that the loudness level is inappropriate for the estimated distance and the determination that the wearer and the second speaker are engaged in conversation, providing a feedback to the wearer;

obtaining additional audio data captured by the one or more audio sensors after obtaining the prosodic information, the additional audio data comprising an additional part of the conversation;

estimating a second distance between the wearer and the second speaker;

analyzing the additional audio data to obtain additional prosodic information associated with the wearer, the additional prosodic information comprises an additional indication of an additional loudness level;

using the estimated second distance between the wearer and the second speaker and the additional indication of the additional loudness level to determine that the additional loudness level is inappropriate for the estimated second distance;

determining an elapsed time since the feedback was provided to the wearer;

when the elapsed time is longer than a selected time duration, in response to the determination that the additional loudness level is inappropriate for the estimated second distance, providing an additional feedback to the wearer; and when the elapsed time is shorter than the selected time duration, forgoing the additional feedback to the wearer.

14. The method of claim 13, wherein the prosodic information comprises information associated with at least one of rhythm of speech, tempo of speech and length of pauses.

15. The method of claim 13, wherein the prosodic information comprises information associated with pitch of voice and stress of voice.

16. The method of claim 13, wherein the prosodic information comprises information associated with loudness of voice.

17. The method of claim 13, wherein the prosodic information comprises information associated with at least one of intonation and tone.

18. The method of claim 13, further comprising:
analyzing the audio data to determine a number of participants in the conversation; and
using the determined number of participants in the conversation in the determination that the loudness level is inappropriate for the estimated distance.

19. The method of claim 13, further comprising:
obtaining contextual information based on positioning data associated with the wearable apparatus; and
using the contextual information in the determination that the loudness level is inappropriate for the estimated distance.

20. The method of claim 13, further comprising:
selecting a presentation region associated with the second speaker; and
based on the prosodic information and the presentation region, presenting a visual indication to the wearer using an augmented reality display device.

21. The method of claim 20, further comprising:
analyzing the audio data to identify a linguistic tone associated with the wearer;
using the identified linguistic tone to select a color scheme; and
using the selected color scheme in the presentation of the visual indicator.

22. The method of claim 13, further comprising:
analyzing the audio data to obtain a second prosodic information associated with the second speaker and at least part of the conversation, the second prosodic information comprises a second indication of a second loudness level;
comparing the indication of the loudness level and the second indication of the second loudness level; and
further basing providing the information to the wearer on a result of the comparison of the loudness level and the second indication of the second loudness level.

23. The method of claim 13, further comprising:
analyzing the audio data to identify the second speaker, therefore obtaining identifying information associated with the second speaker; and
further basing providing the information to the wearer on the identifying information.

24. The method of claim 13, further comprising:
using the prosodic information to estimate an emotional state of the wearer; and
further basing providing the information to the wearer on the estimated emotional state of the wearer.

25. A non-transitory computer readable medium storing data and computer implementable instructions for carrying out a method for processing audio for identifying loudness levels of speakers, the method comprising:
capturing audio data using one or more audio sensors included in a wearable apparatus from an environment of a wearer of the wearable apparatus;
analyzing the audio data to determine that the wearer and a second speaker are engaged in conversation;
analyzing the audio data to obtain prosodic information associated with the wearer and at least part of the conversation, the prosodic information comprises an indication of a loudness level;
estimating a distance between the wearer and the second speaker;
using the estimated distance between the wearer and the second speaker and the indication of the loudness level to determine that the loudness level is inappropriate for the estimated distance;
in response to the determination that the loudness level is inappropriate for the estimated distance and the determination that the wearer and the second speaker are engaged in conversation, providing a feedback to the wearer;
obtaining additional audio data captured by the one or more audio sensors after obtaining the prosodic information, the additional audio data comprising an additional part of the conversation;
estimating a second distance between the wearer and the second speaker;
analyzing the additional audio data to obtain additional prosodic information associated with the wearer, the additional prosodic information comprises an additional indication of an additional loudness level;
using the estimated second distance between the wearer and the second speaker and the additional indication of the additional loudness level to determine that the additional loudness level is inappropriate for the estimated second distance;
determining an elapsed time since the feedback was provided to the wearer;
when the elapsed time is longer than a selected time duration in response to the determination that the additional loudness level is inappropriate for the estimated second distance, providing an additional feedback to the wearer; and when the elapsed time is shorter than the selected time duration, forgoing the additional feedback to the wearer.

* * * * *